United States Patent
Cottingham et al.

(10) Patent No.: US 9,757,469 B2
(45) Date of Patent: Sep. 12, 2017

(54) PHARMACEUTICAL PREPARATION

(75) Inventors: Ian Cottingham, St. Prex (CH); Daniel Plaksin, St. Prex (CH); Jenny Aharanov, St. Prex (CH)

(73) Assignee: Ferring B.V., Hofddorp (NL)

( * ) Notice: Subject to any disclaimer, the term of this patent is extended or adjusted under 35 U.S.C. 154(b) by 269 days.

(21) Appl. No.: 14/008,067

(22) PCT Filed: Mar. 29, 2012

(86) PCT No.: PCT/GB2012/000291
§ 371 (c)(1),
(2), (4) Date: Dec. 2, 2013

(87) PCT Pub. No.: WO2012/131306
PCT Pub. Date: Oct. 4, 2012

(65) Prior Publication Data
US 2014/0088010 A1 Mar. 27, 2014

(30) Foreign Application Priority Data

Mar. 31, 2011 (EP) ..................................... 11160736
Jan. 17, 2012 (EP) ..................................... 12151389

(51) Int. Cl.
A61K 47/48 (2006.01)
(52) U.S. Cl.
CPC ............................. A61K 47/48215 (2013.01)
(58) Field of Classification Search
None
See application file for complete search history.

(56) References Cited

U.S. PATENT DOCUMENTS

| | | | | |
|---|---|---|---|---|
| 4,179,337 A * | 12/1979 | Davis et al. | ................... | 435/181 |
| 4,421,896 A | 12/1983 | Dorman | | |
| 5,929,028 A | 7/1999 | Skrabanja et al. | | |
| 2004/0248784 A1 | 12/2004 | Filicori | | |
| 2005/0085412 A1 | 4/2005 | Loumaye et al. | | |
| 2008/0226681 A1 | 9/2008 | Goletz et al. | | |
| 2008/0242607 A1* | 10/2008 | DeFrees | .......................... | 514/12 |
| 2010/0286067 A1* | 11/2010 | Defrees | ........................ | 514/20.9 |
| 2011/0105398 A1 | 5/2011 | Cottingham et al. | | |
| 2013/0023476 A1 | 1/2013 | Cottingham et al. | | |
| 2014/0249082 A1 | 9/2014 | Cottingham et al. | | |

FOREIGN PATENT DOCUMENTS

| | | |
|---|---|---|
| CN | 1269833 | 10/2000 |
| CN | 1553808 | 12/2004 |
| CN | 1826135 | 8/2006 |
| EP | 0300021 | 1/1989 |
| JP | 2003524015 | 8/2003 |
| JP | 2003526080 | 9/2003 |
| JP | 2005515974 | 6/2005 |
| JP | 2006-526609 | 11/2006 |
| JP | 2007-522179 | 8/2007 |
| JP | 2010-505875 | 2/2010 |
| WO | WO 88/05662 | 8/1988 |
| WO | WO 88/10270 | 12/1988 |
| WO | WO 98/58957 | 12/1998 |
| WO | WO 99/41584 | 8/1999 |
| WO | WO 01/62773 | 8/2001 |
| WO | WO 03/022302 | 3/2003 |
| WO | WO 03/035686 | 5/2003 |
| WO | WO 03/038100 | 5/2003 |
| WO | WO 2004/105788 | 12/2004 |
| WO | WO 2005/076013 | 8/2005 |
| WO | WO 2005/080585 | 9/2005 |
| WO | WO 2008/060780 | 5/2008 |
| WO | WO 2008060780 A2 * | 5/2008 |
| WO | WO 2009/127826 | 10/2009 |
| WO | WO 2011/042688 | 4/2011 |
| WO | WO 2011042688 A1 * | 4/2011 ............. C07K 14/59 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Abidi F E et al., "Lectin-binding assay by polyethylene glyco 8000", Analytical Biochemistry, Academic Press Inc., vol. 166, No. 2, pp. 257-266 (1987).
Zhu K J et al., "Preparation and Characterization of HCG-Loaded Polylactide or Poly (Lactide-co-glycolide) Microspheres using a Modified Water-in-Oil-in-Water (W/O/W) Emulsion Solvent Evaporation Technique", Journal of Microencapsulation, Taylor and Francis, Basingstoke, GB, vol. 18, No. 2, pp. 247-260 (2001).
International Search Report mailed Jul. 30, 2012, which issued in corresponding International Application No. PCT/GB2012/000291.
Amoresano et al., "Structural characterisation of human recombinant glycohormones follitropin, lutropin and choriogonadotropin expressed in Chinese hamster ovary cells," Eur J Biochem., 1996, 242:608-618.
Andersen et al., FSH Isoform Composition of Commercial Gonadotrophin Preparations: a Neglected Aspect? *Reprod. Biomed. Online*, 2004, 9(2), 231-236.
Arey et al., "Induction of promiscuous G protein coupling of the follicle-stimulating hormone (FSH) receptor: a novel mechanism for transducing pleiotropic actions of FSH isoforms", *Mol. Endocrinol.*, 1997, 11(5), 517-26.
Avis, K. E., "Parenteral Preparations—History, Administration, Components, Production, Quality Control, Packaging, Labeling", *Remington's Pharmaceutical Sciences*, fifteenth edition, 1975, 1461-1487.
Baenziger, et al., "Pituitary glycoprotein hormone oligosaccharides: structure, synthesis and function of the asparagine-linked oligosaccharides on lutropin, follitropin and thyrotropin", *Biochim. Biophys. Acta.*, 1988, 947(2), 287-306.
Bassett and Driebergen, "Continued Improvements in the Quality and Consistency of Follitropin Alfa, Recombinant Human FSH", *Reprod. Biomed. Online*, 2005, 10(2) 169-177.
Combarnous, Y., "Structure et relations structure-activité des hormones folliculo-stimulantes recombinantes humaines", *Médecine/Sciences*, 1999, 15, 167-74 (with English translation).

(Continued)

Primary Examiner — Andrea McCollum
(74) Attorney, Agent, or Firm — Fish & Richardson P.C.

(57) ABSTRACT

Polyethylene glycol modified human chorionic gonadotropin (hCG), preparations thereof, compositions thereof, and methods of preparation and use thereof are described.

27 Claims, 8 Drawing Sheets

(56) References Cited

OTHER PUBLICATIONS

Dalpathado et al., "Comparative glycomics of the glycoprotein follicle stimulating hormone: glycopeptide analysis of isolates from two mammalian species", *Biochem.*, 2006, 45(28), 8665-73.

Damián-Matsumura et al., "Oestrogens regulate pituitary alpha2,3-sialyltransferase messenger ribonucleic acid levels in the female rat", *J. Mol. Endocrinol.*, 1999, 23(2), 153-65.

D'Antonio et al., "Biological Characterization of Recombinant Human Follicle Stimulating Hormone Isoforms", *Human Reproduction*, 1999, 14, 1160-1167.

de Leeuw et al., "Structure-function relationship of recombinant follicle stimulating hormone (Puregon®)", *Mol. Hum. Reprod.*, 1996, 2, 361-69.

Deardoff, D. L., "Isotonic Solutions—Freezing Point, Calculations, Tonicity Testing, Methods", *Remington's Pharmaceutical Sciences*, fifteenth edition, 1975, 1405-1412.

Dias, J. A. and Van Roey, P., "Structural biology of human follitropin and its receptor", *Arch. Med. Res.*, 2001, 32(6), 510-19.

Expert Declaration (Exhibit No. 52) and Curriculum Vitae (Exhibit No. 52a) of Yves Combarnous dated Aug. 28, 2009 (27 pgs.).

Fiddes and Goodman, "Isolation, Cloning and Sequence Analysis of the cDNA for the Alpha-Subunit of Human Chorionic Gonadotropin", *Nature*, 1979, 281, 351-356.

Fiddes and Goodman, "The cDNA for the Beta-Subunit of Human Chorionic Gonadotropin Suggests Evolution of a Gene by Readthrough into the 3'-Untranslated Region", *Nature*, 1980, 286, 684-387.

Flack et al., "Increased biological activity due to basic isoforms in recombinant human folliclestimulating hormone produced in a human cell line", *J. Clin. Endocrinol. Metab.*, 1994, 3(79), 756-60.

Fox et al., "Three-dimensional structure of human follicle-stimulating hormone", *Mol. Endocrinol.* 2001, 15(3), 378-89.

Grabenhorst et al., "Construction of stable BHK-21 cells coexpressing human secretory glycoproteins and human Gal(beta 1-4)GlcNAc-R alpha 2,6-sialyltransferase alpha 2,6-linked NeuAc is preferentially attached to the Gal(beta 1-4)GlcNAc(beta 1-2)Man(alpha 1-3)-branch of diantennary oligosaccharides from secreted recombinant beta-trace protein", *Eur. J Biochem.*, 1995, 232(3), 718-25.

Green, E. D. et al., "Asparagine-linked oligosaccharides on lutropin, follitropin, and thyrotropin. II. Distributions of sulfated and sialylated oligosaccharides on bovine, ovine, and human pituitary glycoprotein hormones", *J. Biol. Chem.*, 1988, 263(1), 36-44.

Grundmann et al., "Complete cDNA sequence encoding human beta-galactoside alpha-2,6-sialyltransferase", *G Nucleic Acids Res.*, 1990, 18(3), 667.

Hard et al., "The Carbohydrate Chains of the [beta] Subunit of Human Chorionic Gonadotropin Produced by the Choriocarcinoma Cell Line BeWo. Novel O-linked and Novel Bisecting-GlcNAc-Containing N-linked Carbohydrates", *European Journal of Biochemistry DE*, 1992, 205(2), 1992, 785-798.

Harvey, S. C., "Cardiovascular Drugs—Antihypertensive and Hypotensive Drugs, Peripheral Vasodilators, Coronary Drugs, Cardiac Glycosides, Antiarrhythmic Drugs, Drugs Affecting Blood Lipids, Miscellaneous Drugs", *Remington's Pharmaceutical Sciences*, fifteenth edition, 1975, 807-820.

Harvey, S. C., "Sympathomimetic Drugs", *Remington's Pharmaceutical Sciences*, fifteenth edition, 1975, 780-797.

Horseman et al., "A biological, immunological and physic-chemical comparison of the current clinical batches of the recombinant FSH preparations Gonal-F and Puregon", *Hum. Reprod.*, 2000, 15(9), 1898-1902.

Howles, C. M., "Genetic engineering of human FSH (Gonal-F®)", *Hum. Reprod. Update*, 1996, 2(2), 172-91.

International Search Report dated Jan. 31, 2011 for International Appln. No. PCT/GB2010/001854 (4 pgs.).

International Search Report dated Jun. 30, 2009 for International Appl. No. PCT/GB2009/000978 (8 pgs.).

Jones et al., "High level expression of recombinant IgG in the human cell line Per.C6", *Biotechnol. Progress*, 2003, 19, 163-68.

Kagawa et al., "Comparative Study of the Asparagine-linked Sugar Chains of Natural Human Interferon-beta 1 and Recombinant Human Interferon-beta 1 Produced by Three Different Mammalian Cells", *J. Biol. Chem.*, 1988 263(33), 17508-17515.

Keene et al., "Expression of Biologically active Human Follitropin in Chinese Hamster Ovary Cells", *J Biol. Chem.*, 1989, 264(9), 4769-75.

Kessler et al., "Structure and location of the O-glycosidic carbohydrate units of human chorionic gonadotropin," *J Biol. Chem.*, Aug. 1979, 254(15):7909-7914.

Kitagawa et al., Cloning of a Novel α2,3-Sialyltransferase that Sialylates Glycoprotein and Glycolipid Carbohydrate Groups, *J. Biol. Chem.*, 1994, 269(2), 1394-1401.

Lee et al., "Alteration of terminal glycosylation sequences on N-linked oligosaccharides of Chinese hamster ovary cells by expression of beta-galactoside alpha 2,6-sialyltransferase", *J. Biol. Chem.*, 1989, 264(23), 13848-55.

Lowry et al., "Protein Measurement with the Folin Phenol Reagent", *J. Biol.Chem.*, 1951, 193(1), 265-75.

Lowry et al., "Purification of Anterior Pituitary and Hypothalamic Hormones", *Clin. Pathol. Suppl. (Assoc. Clin. Pathol.)*, 1976, 16-21.

Olijve et al., "Molecular biology and biochemistry of human recombinant follicle stimulating hormone (Puregon®)", *Mol. Hum. Reprod.*, 1996, 2(5), 371-82.

Otto et al., "Sialylated complex-type N-Glycans enhance the signalling activity of soluble intercellular adhesion moledule-1 in mouse astrocytes," *J Biol. Chem.*, 2004, 270(34):35201-35209.

Pierce et al., "Glycoprotein hormones: structure and function", *Ann. Rev. Biochem.*, 1981, 50, 465-95.

Pricer et al., "The binding of desialylated glycoproteins by plasma membranes of rat liver", *J. Biol. Chem.*, 1971, 246(15), 4825-33.

Rathnam et al., "Primary amino acid sequence of follicle-stimulating hormone from human pituitary glands. I. alpha subunit", *J. Biol. Chem.*, 1975, 250(17), 6735-46.

Regoeczi et al., "Elimination of asialofetuin and asialoorosomucoid by the intact rat. Quantitative aspects of the hepatic clearance mechanism", *Biochim. Biophys. Acta.*, 1978, 541(3), 372-84.

Royle et al., "Detailed Structural Analysis of N-Glycans Released From Glycoproteins in SDS-Page Gel Bands Using HPLC Combined With Exoglycosidase Array Digestions", *Methods Mol. Biol.: Glycobiol. Protocols*, 2006, 347, 125-44.

Ryan et al., "Structure-function relationships of gonadotropins", *Recent Prog Horm Res.*, 1987, 43, 383-429.

Saxena et al., "Amino acid sequence of the beta subunit of follicle-stimulating hormone from human pituitary glands", *J. Biol. Chem.*, 1976, 251(4), 993-1005.

Stanton et al., "Application of a sensitive HPLC-based fluorometric assay to determine the sialic acid content of human gonadotropin isoforms," *J. Biochem. Biophys. Methods*, 1995, 30:37-48.

Steelman and Pohley, "Assay of the Follicle Stimulating Hormone Based on the Augmentation with Human Chorionic Gonadotropin", *Endocrinology*, 1953 53(6), 604-616.

Steer et al., "Studies on a mammalian hepatic binding protein specific for asialoglycoproteins. Evidence for receptor recycling in isolated rat hepatocytes", *J. Biol. Chem.*, 1980, 255(7), 3008-13.

Svensson et al., "Organization of the Beta-galactoside Alpha 2,6-sialyltransferase Gene. Evidence for the Transcriptional Regulation of Terminal Glycosylation", *J. Biol. Chem.*, 1990, 265(34):20863-20868.

Swinyard., "Respiratory Drugs—Stimulants, Expectorants, Antitussives, Gases", *Remington's Pharmaceutical Sciences*, fifteenth edition, 1975, 798-806.

Takeuchi et al., "Comparative Study of the Asparagine-linked Sugar Chains of Human Erythropoietins Purified from Urine and the Culture Medium of Recombinant Chinese Hamster Ovary Cells", *J. Biol. Chem.*, 1988, 263(8), 3657-3663.

Timossi et al., "A naturally occurring basically charged human follicle-stimulating hormone (FSH) variant inhibits FSH-induced androgen aromatization and tissue-type plasminogen activator enzyme activity in vitro", *Neuroendocrinol.*, 1998, 67(3), 153-63.

(56) References Cited

OTHER PUBLICATIONS

Timossi et al., "Differential effects of the charge variants of human follicle-stimulating hormone", *J. Endocrinol.*, 2000, 165(2), 193-205.

Ulloa-Aguirre et al., "Biological characterization of the naturally occurring analogues of intrapituitary human follicle stimulating hormone", *Hum. Reprod.*, 1992, 7(1), 23-30.

Ulloa-Aguirre et al., "Endocrine regulation of gonadotropin glycosylation", *Arch. Med. Res.*, 2001, 32(6), 520-32.

Ulloa-Aguirre et al., "Immunological and biological potencies of the different molecular species of gonadotrophins", *Hum. Reprod.*, 1988, 3, 491-501.

Ulloa-Aguirre et al., "Follicle-stimulating Isohormones: Characterization and Physiological Relevance", *Endocr. Rev.*, 1995, 16(6), 765-87.

Ulloa-Aguirre et al., "Impact of Carbohydrate Heterogeneity in Function of Follicle-stimulating Hormone: Studies Derived from in vitro and in vivo models", *Biol. Reprod.*, 2003, 69(2), 379-389.

Van Lenten et al., "The binding of desialylated glycoproteins by plasma membranes of rat liver. Development of a quantitative inhibition assay", *J. Biol. Chem.*, 1972, 247(14), 4633-40.

Wide et al., "Change in electrophoretic mobility of human follicle-stimulating hormone in serum after administration of gonadotropin-releasing hormone", *J. Clin. Endocrinol. Metab.*, 1990, 70, 271-76.

Wide et al., "More basic forms of both human follicle-stimulating hormone and luteinizing hormone in serum at midcycle compared with the follicular or luteal phase", *J. Clin. Endocrinol. Metab.*, 1993, 76, 885-89.

Wide et al., "Sulfonation and sialylation of gonadotropins in women during the menstrual cycle, after menopause, and with polycystic ovarian syndrome and in men", *J. Clin. Endocrinol. Metab.*, 2007, 92(11), 4410-17.

Zambrano et al., "Receptor binding activity and in vitro biological activity of the human FSH charge isoforms as disclosed by heterologous and homologous assay systems: Implications for the structure—function relationship of the FSH variants", *Endocrine*, 1999, 10(2), 113-21.

Zhang et al., "Stable expression of human alpha-2,6-sialyltransferase in Chinese hamster ovary cells: functional consequences for human erythropoietin expression and bioactivity", *Biochim. Biophys. Acta.*, 1998, 1425(3), 441-52.

Kozlowski et al., "Development of Pegylated Interferons for the Treatment of Chronic Hepatitis C", BioDrugs, 2001, 15(7), 419-429.

Japanese Office Action in Japanese Application No. JP 2014-501706, dated Dec. 22, 2015, 5 pages (English Translation).

* cited by examiner hCG expression vector

α2,3-sialyltransferase (ST3GAL4) expression vector

α2,6-sialyltransferase (ST6GAL1) expression vector

Legend:
1. Ovitrelle – 15µg.
2. Ovitrelle – 10µg.
3. Superdex 75-MP (Ref.08009-15) – 10µg.
4. Superdex 75-MP (Ref.08009-15) – 15µg.

PHARMACEUTICAL PREPARATION

The present invention relates to human chorionic gonadotrophin (hCG) for use in the treatment of infertility. In particular it relates to chemical modification, including PEGylation, of human chorionic gonadotrophin (hCG) by which, for example, the chemical and/or physiological properties of hCG may be changed.

The gonadotrophins are a group of heterodimeric glycoprotein hormones which regulate gonadal function in the male and female. They include follicle stimulating hormone (FSH), luteinising hormone (LH) and chorionic gonadotrophin (CG).

Human chorionic gonadotrophin (hCG) is naturally secreted by the anterior pituitary gland and functions to support follicular development and ovulation. hCG comprises a 92 amino acid alpha sub-unit, also common to the other glycoprotein hormones LH and FSH, and a 145 amino acid beta sub-unit unique to hCG, which dictates the hormone specificity. Each sub-unit is post translationally modified by the addition of complex carbohydrate residues. The alpha sub-unit contains 2 N-linked glycosolation sites at amino acids 52 and 78 and the beta sub-unit contains 2 N-linked glycosolation sites at amino acids 13 and 30 and four O-linked glycosylation sites at amino acids 121, 127, 132 and 138.

hCG extracted from the urine of pregnant women [CHORAGON® (Ferring)] has been used for many years in infertility treatment. The production of hCG extracted from urine involves the collection and processing of large amounts of urine. A recombinant version of hCG, OVITRELLE® (Serono), is also available. This is expressed in Chinese hamster ovary (CHO) cells. The known recombinant hCG product has a different pharmacokinetic profile to hCG produced from human urine.

There is considerable heterogeneity associated with hCG preparations which relates to differences in the amounts of various isoforms present. Individual hCG isoforms exhibit identical amino acid sequences but differ in the extent to which they are post-translationally modified; particular isoforms are characterised by heterogeneity of the carbohydrate branch structures and differing amounts of sialic acid (a terminal sugar) incorporation, both of which appear to influence the specific isoform bioactivity.

Glycosylation of natural hCG is highly complex. The glycans in naturally derived pituitary hCG can contain a wide range of structures that can include combinations of bi-, tri- and tetra-antennary glycans. The glycans can carry further modifications: core fucosylation, bisecting glucosamine, chains extended with acetyl galactosamine, partial or complete sialylation, sialylation with $\alpha 2,3$ and $\alpha 2,6$ linkages, and sulphated galactosamine substituted for galactose. Furthermore, there are differences between the distributions of glycan structures at the individual glycosylation sites.

The glycosylation of recombinant hCG ("rhCG") products reflects the range of glycosyltransferases present in the host cell line. The existing rhCG product, OVITRELLE®, is derived from engineered Chinese hamster ovary cells (CHO cells). The range of glycan modifications in CHO derived rhCG are more limited than those found on the natural products, derived from urine. Examples of the reduced glycan heterogeneity found in CHO derived rhCG include a lack of bisecting glucosamine and a reduced content of core fucosylation and acetyl lactosamine extensions. In addition, CHO cells are only able to add sialic acid using the $\alpha 2,3$ linkage (Kagawa et al, 1988, Takeuchi et al, 1988, Svensson et al., 1990). This is different from naturally produced hCG which contains glycans with a mixture of $\alpha 2,3$ and $\alpha 2,6$-linked sialic acid.

It has been demonstrated that a recombinant FSH preparation (Organon) differs in the amounts of FSH with an isoelectric point (pI) of below 4 (considered the acidic isoforms) when compared to pituitary, serum or post-menopausal urine FSH (Ulloa-Aguirre et al. 1995). The amount of acidic isoforms in the urinary preparations of FSH was much higher as compared to the recombinant products, GONAL-F® (Serono) and PUREGON® (Organon) (Andersen et al. 2004). This must reflect a lower molar content of sialic acid in rFSH since the content of negatively-charged glycan modified with sulphate is low in FSH. The lower sialic acid content, compared to natural FSH, is a feature of both commercially available FSH products and therefore must reflect a limitation in the manufacturing process (Bassett and Driebergen, 2005). The circulatory life-time of FSH has been documented for materials from a variety of sources. Some of these materials have been fractionated on the basis of overall molecular charge, as characterised by their pI, in which more acid equates to a higher negative charge. The major contributor to overall molecular charge is the total sialic content of each FSH molecule. For instance, rFSH (Organon) has a sialic acid content of around 8 mol/mol, whereas urine-derived FSH has a higher sialic acid content (de Leeuw et al. 1996). The corresponding plasma clearance rates in the rat are 0.34 and 0.14 ml/min (Ulloa-Aguirre et al. 2003). In another example where a sample of recombinant FSH was split into high and low pI fractions, the in vivo potency of the high pI (lower sialic acid content) fraction was decreased and it had a shorter plasma half-life (D'Antonio et al. 1999). The applicants have found that, similar to FSH, the known, CHO derived, recombinant hCG product (e.g. OVITRELLE®) also has a lower amount of hCG with an isoelectric point (pI) of below 4 (considered the acidic isoforms) than urinary hCG, also reflecting a lower sialic acid content of the known rhCG product compared to urinary hCG.

The total sialic acid content of hCG and rhCG is not directly comparable since sialic acids are commonly linked in two ways. Pituitary/serum/urinary hCG contain both $\alpha 2,3$ and $\alpha 2,6$-linked sialic acid, with a predominance of the former. However, CHO cell derived recombinants only contain $\alpha 2,3$ (Kagawa et al, 1988, Takeuchi et al, 1988, Svensson et al., 1990). In other words, recombinant proteins expressed using the CHO system will differ from their natural counterparts in their type of terminal sialic acid linkages. This is another difference between natural and current recombinant products in addition to the lower overall sialic acid content of the latter, and is an important consideration in the production of biologicals for pharmaceutical use since the carbohydrate moieties may contribute to the pharmacological attributes of the molecule.

It is therefore desirable to have a rhCG product that more closely replicates or mimics the physiochemical and pharmacokinetic profile of the product produced from human urine. It is desirable to have a rhCG product that has improved pharmacokinetic property or properties compared to the known recombinant product.

The applicants have developed a human derived recombinant hCG which has a more acidic profile than the CHO derived product, OVITRELLE®, and which has a higher sialic acid content. The applicants' research indicates that the type of sialic acid linkage, $\alpha 2,3$- or $\alpha 2,6$-, can have a dramatic influence on biological clearance of hCG. Human cell lines, as opposed to CHO cell lines, can express recombinant hCG with sialic acids attached by both α2,3 and α2,6 linkages.

Recombinant hCG with a mixture of both α2,3 and α2,6-linked sialic acid was made by engineering a human cell line to express both rhCG and α2,3 sialyltransferase. The expressed product is highly acidic and carries a mix of both α2,3- and α2,6-linked sialic acids; the latter provided by the endogenous sialyltransferase activity. This has two advantages over rhCG expressed in conventional CHO cells: first the material is more highly sialylated due to the combined activities of the two sialyltransferases; and secondly the material more closely resembles the natural hCG. This is likely to be more biologically appropriate compared to CHO cell derived recombinant products that have produce only α2,3 linked sialic acid and have decreased sialic acid content. This is the subject of International patent application No. PCT/GB2010/001854. The applicants have surprisingly found that their human derived recombinant hCG may more closely replicate or mimic the physiochemical and pharmacokinetic profile of the natural human urinary product than other recombinant products. In other words, rhCG of the invention may be closer to the "natural" hCG. This may have significant advantages regarding dosing etc. Further, a more "natural" or more "human" product may be more desirable to the patient, who may desire therapy, although in a sense artificial, to be as "natural" as possible.

It is generally known that chemical modification of therapeutic proteins, for example with water soluble polymers, may have the result of changing the chemical and/or physiological properties of the protein (e.g. decreasing the clearance rate, improving stability etc., thereby extending the time of activity). One such class of water soluble polymers is poly (alkylene oxide), for example poly (ethylene glycol) (PEG). Indeed, the term "PEGylate" or "pegylate" has been coined to refer to modification (attachment) of at least one PEG molecule to a chemical entity. Methods for attachment of certain poly (ethylene glycol) moieties are available, for example Roberts M. J. et al., *Adv. Drug Del. Rev.* 54: 459-476,2002; Harris J. M. et al., *Drug Delivery Sytems* 40: 538-551,2001. PEGylated therapeutic proteins have been described, for example ADAGEN® (PEGylated formulation of adenosine deaminase for treating severe combined immunodeficiency disease) and ONCASPAR® (PEGylated L-asparaginase for treating hypersensitive ALL patients). However, PEGylated forms of hCG, especially those with the appropriate properties to be a commercial product, are hitherto unavailable.

According to the present invention there is provided a poly (ethylene glycol) modified hCG. Preferably the poly (ethylene glycol) modified hCG has formula (Ia)

$$(R)_n\text{—}X\text{—}Y \quad (Ia);$$

wherein: (R) is a polyethylene glycol PEG or a methoxypoly (ethylene glycol) (mPEG); n is 1, 2, 3 or 4; X is a bond or a linker group; and Y is hCG or agonist variant thereof. Preferably, n is 1 and X is a covalent bond, or n is 1, 2 or 4 and X is a linker group. Preferably the linker group X is bonded at one end to the N-terminus of the hCG.

The linker group X is a moiety which links the hCG (e.g. which is bound at one end to the hCG, for example which is bound at one end to the N-terminus of the hCG) to the (or each) R group (e.g. which is also bound to the or each R group, for example which is also bound to a terminal oxygen of or each R group). The linker group X may be any linker molecule known in the field of PEGylation.

The linker group X may be, for example, O or —C(=O)— or —(CH$_2$)$_t$—C(=O)— wherein t is 0 or an integer from 1 to 10.

The linker group X may be, for example, of a group of formula (Z$^1$CH$_2$)$_b$—(CH$_2$)$_z$—(CHZ$^2$)$_a$—(CH$_2$)$_u$—O—C(=O)—NH—(CH$_2$)$_t$—C(=O)— wherein: —C(=O)— is bound to Y; Z$^1$ and Z$^2$ represent a bond to an R group; a and b are each independently selected from 0 and 1 provided that a and b are not both 0; t, u and z are each independently selected from 0 or an integer from 1 to 10.

In some examples, a, b and u are 1; t is 2 and z is 0, so X is Z$^1$CH$_2$—CHZ$^2$—CH$_2$—O—C(=O)—NH—(CH$_2$)$_2$—C(=O)—, and the poly (ethylene glycol) modified hCG has formula CH$_2$R—CHR—CH$_2$—O—C(=O)—NH—(CH$_2$)$_2$—C(=O)-hCG, wherein each R is a polyethylene glycol PEG or a methoxypoly (ethylene glycol) (mPEG). In a preferred example each R is a methoxypoly (ethylene glycol) (mPEG) (see Example 12A).

The linker group X may be, for example, of a group of formula (Z$^1$CH$_2$)$_b$—(CH$_2$)$_z$—(CHZ$^2$)$_a$—(CH$_2$)$_u$—O—C(=O)—NH—(CH$_2$)$_t$—C(=O)— wherein: —C(=O)— is bound to Y; a and b are each independently selected from 0 and 1; t, u and z are each independently selected from 0 or an integer from 1 to 10; and Z$^1$ and Z$^2$ are each independently selected from (Z$^3$CH$_2$)$_d$—(CH$_2$)$_e$—(CHZ$^4$)$_c$—(CH$_2$)$_f$—O(CH$_2$CH$_2$O)$_m$ wherein Z$^3$ and Z$^4$ represent a bond to an R group; c and d are each independently selected from 0 and 1; e and f are independently selected from 0 or an integer from 1 to 10, and m is 1 to 20, for example 1 to 10.

In some examples, a and b and u are 1, t is 2 and z is 0; Z$_1$=Z$^2$ and are both (Z$^3$CH$_2$)$_d$—(CH$_2$)$_e$—(CHZ$^4$)$_c$—(CH$_2$)$_f$—O(CH$_2$CH$_2$O)$_m$ wherein c, d and f are 1, e is 0 and Z$^3$ and Z$^4$ represent a bond to an R group; so X is [CH$_2$R—CHR—CH$_2$—O(CH$_2$CH$_2$O)$_m$]—CH$_2$—CH[CH$_2$R—CHR—CH$_2$—O(CH$_2$CH$_2$O)$_m$]—CH$_2$—O—C(=O)—NH—(CH$_2$)$_2$—C(=O)—, and the poly (ethylene glycol) modified hCG has structure:

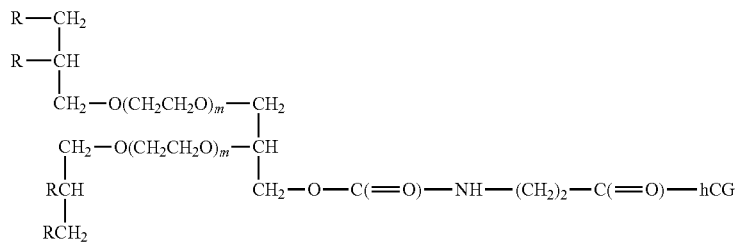

(that is [CH$_2$R—CHR—CH$_2$—O(CH$_2$CH$_2$O)$_m$]—CH$_2$—CH[CH$_2$R—CHR—CH$_2$—O(CH$_2$CH$_2$O)$_m$]—CH$_2$—O—C(=O)—NH—(CH$_2$)$_2$—C(=O)-hCG), wherein each R is a polyethylene glycol PEG or a methoxypoly (ethylene glycol) (mPEG). In a preferred example each R is methoxypoly (ethylene glycol) (mPEG).

The linker group X may be, for example, of a group of formula —R$^3$-R$^2$-R$^1$—C(=O)— wherein: —C(=O)— is bound to Y; R$^1$ is a bond, or an optionally substituted branched or straight chain C$_1$ to C$_{10}$ alkyl group which is bound to R or at least one R if more than one R is present, and R$^2$ and R$^3$ are each independently selected from a bond H, or an optionally substituted branched or straight chain C$_1$ to C$_{10}$ alkyl group bound to one or more R groups.

hCG can be obtained by any means known in the art. hCG as used herein includes human-derived and recombinant hCG. Human-derived hCG can be purified from any appropriate source (e.g. urine) by any method known in the art. The hCG may be recombinant hCG—for example expressed in a human cell line. Methods of expressing and purifying recombinant hCG are well known in the art. Preferably the hCG is a recombinant hCG ("rhCG" or "rechCG"). Preferably the hCG is a human cell line derived recombinant hCG.

According to the present invention in a further aspect there is provided a pharmaceutical preparation comprising a poly (ethylene glycol) modified hCG, preferably a poly (ethylene glycol) modified hCG of Formula Ia above, preferably a poly (ethylene glycol) modified recombinant hCG, preferably a human cell line derived recombinant hCG. Preferably the hCG is a poly (ethylene glycol) modified, human cell line derived, recombinant hCG.

The invention may therefore provide a poly (ethylene glycol) modified recombinant version of hCG which carries a mix of α2,3 and α2,6 sialic acid.

The compositions of the present invention are preferably prepared from poly(alkylene oxides) that are water soluble at room temperatures. Within this group are alpha-substituted polyalkylene oxide derivatives such as polyethylene glycols (PEGs) and methoxypoly (ethylene glycols) (mPEGs) or other suitable alkyl substituted PAO derivatives such as those containing mono or bis terminal C1-C4 groups. Straight-chained non-antigenic polymers such as monomethyl PEG homopolymers are preferred. Other suitable polyalkylene oxides include other poly(ethylene glycol) homopolymers, other alkyl-poly(ethylene oxide) block copolymers, and copolymers of block copolymers of poly (alkylene oxides).

The or at least one R is a poly(alkylene oxide), for example a polyethylene glycol PEG or a methoxypoly (ethylene glycol) (mPEG), may have a molecular weight between about 200 and about 40,000, for example a molecular weight between 200 and about 20,000, for example a molecular weight between 2,000 and about 10,000, for example a molecular weight of about 5,000.

The poly(ethylene glycol) may be conjugated to the (e.g. recombinant) hCG at an amino acid residue. The poly (ethylene glycol) may be conjugated to the (e.g. recombinant) hCG at the N— amino terminus of the (e.g. recombinant) hCG and/or the C— amino terminus of the (e.g. recombinant) hCG. Preferably 90% or greater of the poly (ethylene glycol) is conjugated to the N-amino terminus of the (e.g. recombinant) hCG. Preferably 95% or greater of the poly (ethylene glycol) is conjugated to the N-amino terminus of the (e.g. recombinant) hCG. It is expected that the use of this poly (ethylene glycol) modified hCG of the invention and/or preparations of the invention for controlled ovarian stimulation, in IVF techniques, and ovulation induction will combine a more natural stimulation of the ovary compared to existing recombinant products with enhanced pharmacokinetic profile. The present invention may further provide PEG-hCG and mPEG-hCG conjugates having one or two PEG or mPEG molecule(s) (or a linker molecule including one, two or more PEG or mPEG molecules) attached predominately at the N-terminal of the hCG. This avoids or reduces problems associated with a heterogeneous product caused by PEGylation at different sites on different hCG molecules. It will be appreciated that the PEG-hCG and mPEG-hCG conjugates of the invention may have one or two PEG or mPEG molecules attached at the N-terminal of the hCG by means of covalent bonds. If a linker molecule is attached at the N-terminal, the linker molecule may bear one, two or more PEG or mPEG molecules.

According to the present invention in a further aspect there is provided a composition comprising a modified hCG of formula (I):

$$(R)_n—X—Y \qquad (I)$$

wherein:
R is a water soluble, substantially non-antigenic polymer;
n is 1, 2, 3 or 4;
X is a bond or a linker group; and
Y is hCG or agonist variant thereof.

Preferably, n is 1 and X is a covalent bond, or n is 1, 2 or 4 and X is a linker group. The or at least one R is a straight-chained polymer, for example a poly(alkylene oxide), for example a polyethylene glycol PEG or a methoxypoly (ethylene glycol) (mPEG). Preferably the linker group X is bonded at one end to the N-terminus of the hCG.

The linker group X is a moiety which links the hCG (e.g. which is bound at one end to the hCG, for example which is bound at one end to the N-terminus of the hCG) to the (or each) R group (e.g. which is also bound to the or each R group, for example which is also bound to a terminal oxygen of or each R group). The linker group X may be any linker molecule known in the field of PEGylation.

The linker group X may be, for example, O or —C(=O)— or —(CH$_2$)$_t$—C(=O)— wherein t is 0 or an integer from 1 to 10.

The linker group X may be, for example, of a group of formula (Z$^1$CH$_2$)$_b$—(CH$_2$)$_z$—(CHZ$^2$)$_a$—(CH$_2$)$_u$—O—C(=O)—NH—(CH$_2$)$_t$—C(=O)— wherein: —C(=O)— is bound to Y; Z$^1$ and Z$^2$ represent a bond to an R group; a and b are each independently selected from 0 and 1 provided that a and b are not both 0; t, u and z are each independently selected from 0 or an integer from 1 to 10.

In some examples, a, b and u are 1; t is 2 and z is 0, so X is Z$^1$CH$_2$—CHZ$^2$—CH$_2$—O—C(=O)—NH—(CH$_2$)$_2$—C(=O)—, and the modified hCG has formula CH$_2$R—CHR—CH$_2$—O—C(=O)—NH—(CH$_2$)$_2$—C(=O)-hCG. Each R may be a polyethylene glycol PEG or a methoxypoly (ethylene glycol) (mPEG). In a preferred example each R is a methoxypoly (ethylene glycol) (mPEG) (see Example 12A).

The linker group X may be, for example, of a group of formula (Z$^1$CH$_2$)$_b$—(CH$_2$)$_z$—(CHZ$^2$)$_a$—(CH$_2$)$_u$—O—C(=O)—NH—(CH$_2$)$_t$—C(=O)— wherein: —C(=O)— is bound to Y; a and b are each independently selected from 0 and 1; t, u and z are each independently selected from 0 or an integer from 1 to 10; and Z$^1$ and Z$^2$ are each independently selected from (Z$^3$CH$_2$)$_d$—(CH$_2$)$_e$—(CHZ$^4$)$_c$—(CH$_2$)$_f$—O(CH$_2$CH$_2$O)$_m$ wherein Z$^3$ and Z$^4$ represent a bond to an R group; c and d are each independently selected from 0 and 1; e and f are independently selected from 0 or an integer from 1 to 10, and m is 1 to 20, for example 1 to 10.

In some examples, a and b and u are 1, t is 2 and z is 0; $Z^1=Z^2$ and are both $(Z^3CH_2)_d-(CH_2)_e-(CHZ^4)_c-(CH_2)_f-O(CH_2CH_2O)_m$ wherein c, d and f are 1, e is 0 and $Z^3$ and $Z^4$ represent a bond to an R group; so X is $[CH_2R-CHR-CH_2-O(CH_2CH_2O)_m]-CH_2-CH[CH_2R-CHR-CH_2-O(CH_2CH_2O)_m]-CH_2-O-C(=O)-NH-(CH_2)_2-C(=O)-$, and the modified hCG has structure:

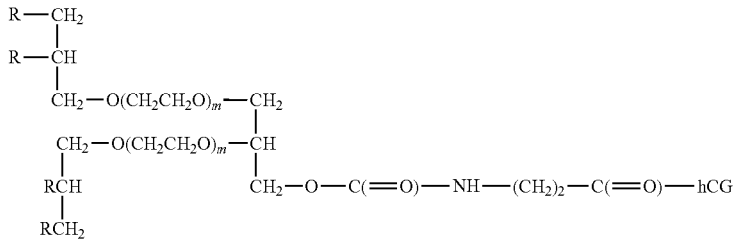

(that is $[CH_2R-CHR-CH_2-O(CH_2CH_2O)_m]-CH_2-CH[CH_2R-CHR-CH_2-O(CH_2CH_2O)_m]-CH_2-O-C(=O)-NH-(CH_2)_2-C(=O)$-hCG). Each R may be a polyethylene glycol PEG or a methoxypoly (ethylene glycol) (mPEG). In a preferred example each R is methoxypoly (ethylene glycol) (mPEG).

The linker group X may be, for example, of a group of formula $-R^3-R^2-R^1-C(=O)-$ wherein: $-C(=O)-$ is bound to Y; $R^1$ is a bond, or an optionally substituted branched or straight chain $C_1$ to $C_{10}$ alkyl group which is bound to R or at least one R if more than one R is present, and $R^2$ and $R^3$ are each independently selected from a bond H or an optionally substituted branched or straight chain $C_1$ to $C_{10}$ alkyl group bound to one or more R groups.

The compositions of the present invention are preferably prepared from poly(alkylene oxides) that are water soluble at room temperatures. Within this group are alpha-substituted polyalkylene oxide derivatives such as polyethylene glycols (PEGs) and methoxypoly (ethylene glycols) (mPEGs) or other suitable alkyl substituted PAO derivatives such as those containing mono or bis terminal C1-C4 groups. Straight-chained non-antigenic polymers such as monomethyl PEG homopolymers are preferred. Other suitable polyalkylene oxides include other poly(ethylene glycol) homopolymers, other alkyl-poly(ethylene oxide) block copolymers, and copolymers of block copolymers of poly(alkylene oxides.

The or at least one R is a poly(alkylene oxide), for example a polyethylene glycol PEG or a methoxypoly (ethylene glycol) (mPEG), may have a molecular weight between about 200 and about 40,000, for example a molecular weight between 200 and about 20,000, for example a molecular weight between 2,000 and about 10,000, for example a molecular weight of about 5,000.

hCG can be obtained by any means known in the art. hCG as used herein includes human-derived and recombinant hCG. Human-derived hCG can be purified from any appropriate source (e.g. urine) by any method known in the art. The hCG may be recombinant hCG—for example expressed in a human cell line. Methods of expressing and purifying recombinant hCG are well known in the art. Preferably the hCG is a recombinant hCG ("rhCG" or "rechCG"). Preferably the hCG is a human cell line derived recombinant hCG.

Preferably the poly (ethylene glycol) modified recombinant hCG includes α2,3 sialylation and α2,6 sialylation. The rhCG may optionally further include α2,8 sialylation.

In embodiments of the invention, the rhCG may be present as a single isoform or as a mixture of isoforms.

The rhCG may have a sialic acid content [expressed in terms of a ratio of moles of sialic acid to moles of protein] of 15 mol/mol or greater (Example 8), for example of from 15 mol/mol to 25 mol/mol, for example from 17 mol/mol to 24 mol/mol, for example from 17.7 mol/mol to 23 mol/mol, for example from 18 mol/mol to 22 mol/mol, for example from 19 mol/mol to 21 mol/mol, for example from 19 mol/mol to 20 mol/mol. The rhCG may be produced or expressed in a human cell line.

The rhCG may have 10% or more of the total sialylation being α2,3-sialylation. For example, 20, 30, 40, 45, 50, 55, 60, 70, 80 or 90% or more of the total sialylation may be α2,3-sialylation. The rhCG may include α2,3-sialylation in an amount which is from 45% to 80% of the total sialylation, for example 50% to 70% of the total sialylation, for example 55 to 65% of the total sialylation. The rhCG may include α2,3-sialylation in an amount which is from 65 to 85% of the total sialylation, for example from 70 to 80% of the total sialylation, for example from 71 to 79% of the total sialylation. The may have 50% or less of the total sialylation being α2,6-sialylation. For example 45, 40, 30, 20, 10, 5% or less of the total sialylation may be α2,6-sialylation. The rhCG may include α2,6-sialylation in an amount which is from 20-55% of the total sialylation, for example, 30-50% of the total sialylation, for example 35-45% of the total sialylation. The rhCG may include α2,6-sialylation in an amount which is from 15 to 35% of the total sialylation, for example from 20 to 30% of the total sialylation, for example from 21 to 29% of the total sialylation. The rhCG may have 5% or less of the total sialylation being α2,8-sialylation. For example 2.5% or less of the total sialylation may be α2,8-sialylation. The rhCG may include α2,8-sialylation in an amount which is from 0 to 4% of the total sialylation, for example 0.1 to 4% of the total sialylation, for example from 0.5 to 3% of the total sialylation, for example from 0.5 to 2.5% of the total sialylation. The rhCG (may have no α2,8-sialylation. By sialylation it is meant the amount of sialic residues present on the hCG carbohydrate structures. α2,3-sialylation means sialylation at the 2,3 position (as is well known in the art) and α2,6 sialylation at the 2,6 position (also well known in the art). Thus "% of the total sialylation may be α 2,3 sialylation" refers to the % of the total number of sialic acid residues present in the hCG which are sialyiated in the 2,3 position. The term "% of the total sialylation being α2,6-sialylation" refers to the % of the total number of sialic acid residues present in the hCG which are sialylated in the 2,6 position.

The rhCG (may have a sialic acid content (amount of sialylation per hCG molecule) of (based on the mass of protein, rather than the mass of protein plus carbohydrate) of 6% or greater (e.g. between 6% and 15%, e.g. between 7% and 13%, e.g. between 8% and 12%, e.g. between 11% and 15%, e.g. between 12% and 14%) by mass.

Recombinant hCG expressed in Chinese hamster ovary (CHO) cells includes exclusively α 2, 3 sialylation.

The rhCG may be produced or expressed in a human cell line. This may simplify (and render more efficient) the production method because manipulation and control of e.g. the cell growth medium to retain sialylation may be less critical than with known processes. The method may also be more efficient because there is less basic rhCG produced than in production of known rhCG products; more acidic rhCG is produced and separation/removal of basic hCG is less problematic. The rhCG may be produced or expressed in a PER.C6® cell line, a PER.C6® derived cell line or a modified PER.C6® cell line. The cell line may be modified using α2,3-sialyltransferase. The rhCG may include α2,6-linked sialic acids (α2,6 sialylation) provided by endogenous sialyltransferase activity [of the cell line]. Alternatively or additionally, the cell line may be modified using α2,6-sialyltransferase.

The rhCG may be produced using α2,3-sialyltransferase. The rhCG may include α2,6-linked sialic acids (α2,6 sialylation) provided by endogenous sialyltransferase activity. The rhCG may be produced using α2,3- and/or α2,6-sialyltransferase.

The rhCG structure contains glycan moieties. Branching can occur with the result that the glycan may have 1, 2, 3, 4 or more terminal sugar residues or "antennae", as is well known in the art. The rhCG of the invention may have glycans with sialylation presence on mono-antennary and/or di-antennary and/or tri-antennary and/or tetra-antennary structures. The rhCG may include mono-sialylated, di-sialylated, tri-sialylated and tetra-sialylated glycan structures, for example with relative amounts as follows: 0.1-4% mono-sialylated; 35-45% di-sialylated; 0.5-8% tri-sialylated and 0-1% tetra-sialylated (e.g. as shown by WAX analysis of charged glycans, as set out in Example 8 D). Preferably, the recombinant hCG of the invention includes mono (1S), di(2S), tri(3S) and tetra(4S) sialylated structures. Preferably, the relative amounts of sialylated structures are in the following ratios (1S:2S:4S:4S): 0.2-1%:35-40%:2.5-7%: 0.5-1% (e.g. as shown by WAX analysis of charged glycans, as set out in Example 8 D).

In an example of the present invention, poly (ethylene glycol) is (e.g. covalently) bound through amino acid residues of hCG (or agonist variant thereof). Preferably the poly (ethylene glycol) is bound to the N-terminus of the hCG. A number of activated poly (ethylene glycol)s having a number of different functional groups, linkers, configurations, and molecular weights are known to one skilled in the art. These may be used to synthesise PEG-hCG conjugates or PEG-hCG agonist variant conjugates, by methods which are known in the art (see e.g. Roberts M. J. et al., Adv. Drug Del. Rev. 54: 459-476, 2002), Harris J. M. et al., Drug Delivery Sytems 40: 538-551, 2001).

According to the present invention in a further aspect there is provided a pharmaceutical composition comprising poly (ethylene glycol) modified recombinant rhCG, for example a poly (ethylene glycol) modified recombinant rhCG including α2,3-sialylation and α2,6-sialylation (e.g. as set out above). The pharmaceutical composition may further comprise FSH and/or LH.

FSH can be obtained by any means known in the art. FSH as used herein includes human-derived and recombinant FSH. Human-derived FSH can be purified from any appropriate source (e.g. urine) by any method known in the art. The FSH may be recombinant FSH—for example expressed in a human cell line. Methods of expressing and purifying recombinant FSH are well known in the art.

LH can be obtained by any means known in the art. LH, as used herein, includes human-derived and recombinant LH. Human-derived LH can be purified from any appropriate source (e.g. urine) by any method known in the art. Methods of expressing and purifying recombinant LH are known in the art.

The pharmaceutical composition may be for the treatment of infertility, e.g. for use in e.g. assisted reproductive technologies (ART), ovulation induction or intrauterine insemination (IUD. The pharmaceutical composition may be used, for example, in medical indications where known hCG preparations are used. The present invention also provides the use of poly (ethylene glycol) modified recombinant rhCG and/or a poly (ethylene glycol) modified recombinant rhCG preparation described herein (according to aspects of the invention) for, or in the manufacture of a medicament for, the treatment of infertility. The pharmaceutical compositions of the present invention can be formulated into well-known compositions for any route of drug administration, e.g. oral, rectal, parenteral, transdermal (e.g. patch technology), intravenous, intramuscular, subcutaneous, intrasusternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

The compositions of the present invention also can contain additives such as but not limited to preservatives, wetting agents, emulsifying agents, and dispersing agents. Antibacterial and antifungal agents can be included to prevent growth of microbes and includes, for example, paraben, chlorobutanol, phenol, sorbic acid, and the like. Furthermore, it may be desirable to include isotonic agents such as sugars, sodium chloride, and the like.

In some cases, to effect prolonged action it is desirable to slow the absorption of hCG (and other active ingredients, if present) from subcutaneous or intramuscular injection. This can be accomplished by the use of a liquid suspension of crystalline or amorphous material with poor water solubility. The rate of absorption of hCG then depends upon its rate of dissolution which, in turn, can depend upon crystal size and crystalline form. Alternatively, delayed absorption of a parenterally administered hCG combination form is accomplished by dissolving or suspending the hCG combination in an oil vehicle.

Injectable depot forms can be made by forming microencapsule matrices of the poly (ethylene glycol) modified recombinant rhCG (and other agents, if present) in biodegradable polymers such as polylactide-polyglycolide. Depending upon the ratio of hCG to polymer and the nature of the particular polymer employed, the rate of hCG release can be controlled. Examples of other biodegradable polymers include polyvinylpyrrolidone, poly(orthoesters), poly (anhydrides) etc. Depot injectable formulations are also prepared by entrapping the hCG in liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

Injectable formulations can be supplied as a product having pharmaceutical compositions containing poly (ethylene glycol) modified recombinant rhCG (optionally with FSH, LH etc.) If there is more than one active ingredient (i.e. poly (ethylene glycol) modified recombinant rhCG and e.g. FSH or LH) these may be suitable for administration separately or together. If administered separately, administration can be sequential. The product can be supplied in any appropriate package. For example, a product can contain a number of pre-filled syringes containing either hCG, FSH, or a combination of both FSH and hCG, the syringes packaged in a blister package or other means to maintain sterility. A product can optionally contain instructions for using the poly (ethylene glycol) modified recombinant rhCG and FSH formulations.

The pH and exact concentration of the various components of the pharmaceutical composition are adjusted in accordance with routine practice in this field. See GOODMAN and GILMAN's THE PHARMACOLOGICAL BASIS FOR THERAPEUTICS, $7^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

DETAILED DESCRIPTION OF THE INVENTION

The present invention will now be described in more detail with reference to the following Examples and to the attached drawings in which.

SEQUENCE SELECTION

Human hCG

The coding region of the gene for the hCG alpha polypeptide was used according to Fiddes and Goodman (1979). The sequence is banked as AH007338 and at the time of construction there were no other variants of this protein sequence. The sequence is referred to herein as SEQ ID NO:1.

The coding region of the gene for hCG beta polypeptide was used according to Fiddes and Goodman (1980). The sequence is banked as NP_000728 and is consistent with the protein sequences of CGbeta3, CGbeta5 and CGbeta7. The sequence is referred herein as SEQ ID NO: 3

Sialyltransferase

α2,3-Sialyltransferase—The coding region of the gene for beta-galactoside alpha-2,3-sialyltransferase 4 (α2,3-sialyltransferase, ST3GAL4) was used according to Kitagawa and Paulson (1994). The sequence is banked as L23767 and referred herein as SEQ ID NO: 5.

α2,6-Sialyltransferase—The coding region of the gene for beta-galactosamide alpha-2,6-sialyltransferase 1 (α2,6-sialyltransferase, ST6GAL1) was used according to Grundmann et al. (1990). The sequence is banked as NM_003032 and referred herein as SEQ ID NO: 7.

Plasmids

Figure 1:
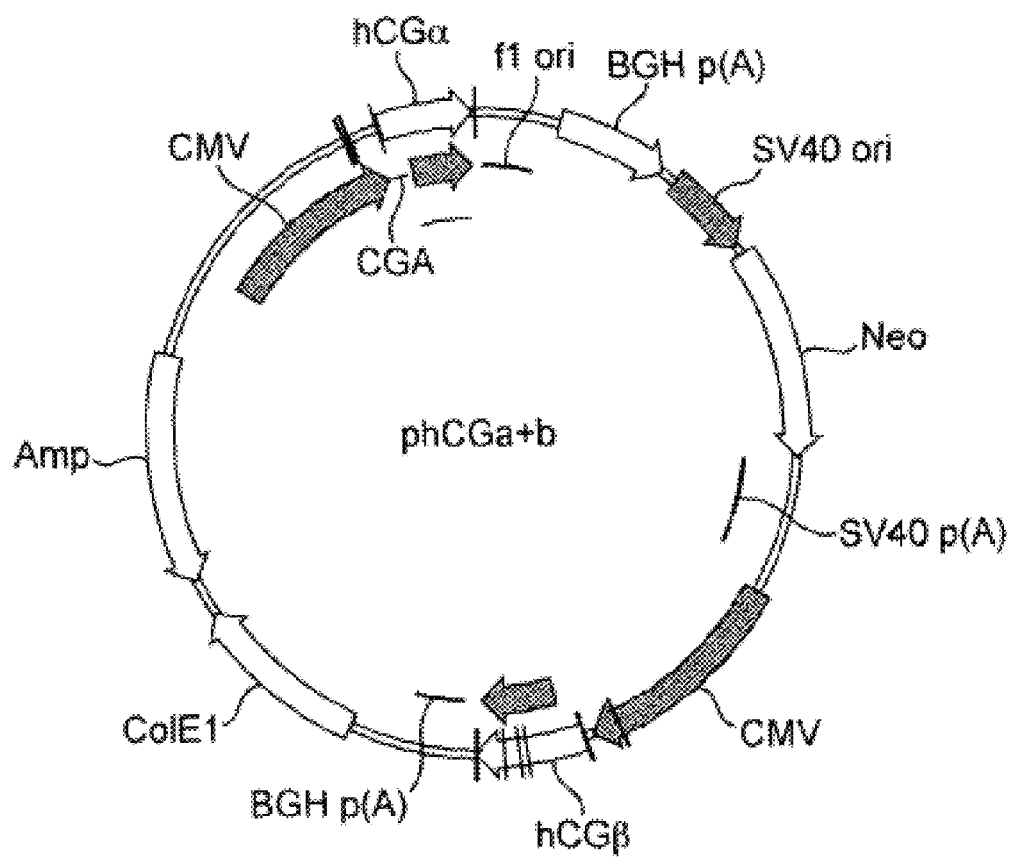
FIG. 1 shows a plasmid map of the phCGalpha/beta expression vector.
Figure 2:
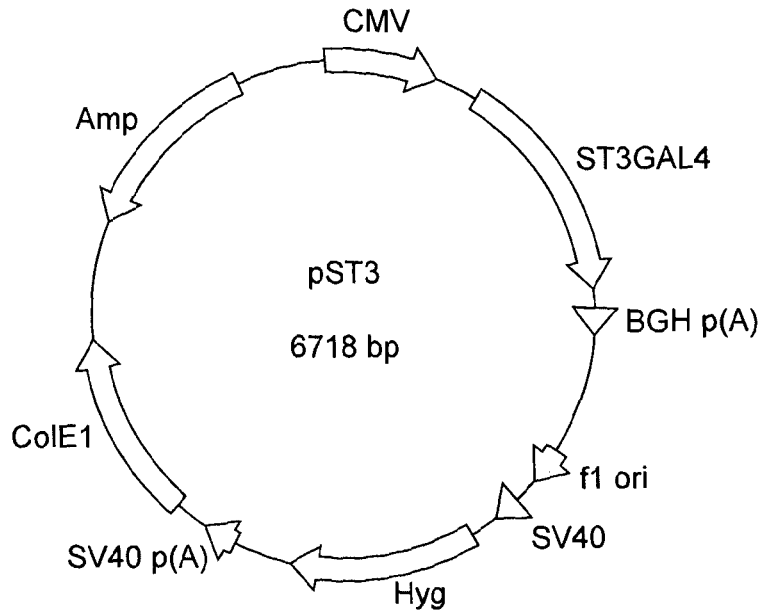
FIG. 2 shows the α2,3-sialyltransferase (ST3GAL4) expression vector.
Figure 3:
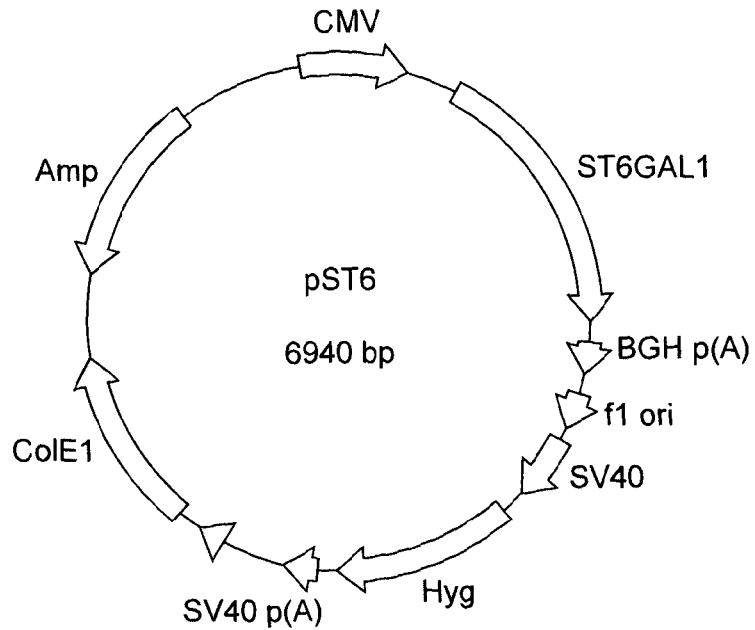
FIG. 3 shows the α2,6-sialyltransferase (ST6GAL1) expression vector.

FIGS. 1, 2 and 3 are plasmid maps of the phCGalpha/beta, pST3 and pST6 expression vectors described in greater detail below. CMV=Cytomegalovirus promoter, BGHp (A)=Bovine Growth Hormone poly-adenylation sequence, fl ori=fl origin of replication, SV40=Simian Virus 40 promoter, Neo=Neomycin resistance marker, Hyg=Hygromycin resistance marker, SV40 p(A)=Simian Virus 40 poly-adenylation sequence, hCG α=human chorionic gonadotropin alpha polypeptide, hCG β=human chorionic gonadotropin beta polypeptide, ST3GAL4=α2,3-sialyltransferase, ST6GAL1=α2,6-sialyltransferase, ColE1=ColE1 origin of replication, Amp=ampicillin resistance marker.

EXAMPLES

Example 1

Construction of the hCG Expression Vector

The coding sequence of hCG alpha polypeptide (AH007338, SEQ ID NO: 1) and hCG beta polypeptide (NP_000728, SEQ ID NO: 3) were amplified by PCR using the primer combinations CGa-fw and CGa-rev and CGb-fw and CGb-rec respectively.

```
                                          (SEQ ID NO: 9)
CGa-fw
5'-CCAGGATCCGCCACCATGGATTACTACAGAAAAATATGC-3'

(SEQ ID NO: 10)
CGa-rev
5'-GGATGGCTAGCTTAAGATTTGTGATAATAAC-3'

(SEQ ID NO: 11)
CGb-fw
5'-CCAGGCGCGCCACCATGGAGATGTTCCAGGGGCTGC-3'
```

-continued

CGb-rev (SEQ ID NO: 12)
5'-CCGGGTTAACTTATTGTGGGAGGATCGGGG-3'

The resulting amplified hCG beta DNA was digested with the restriction enzymes AscI and HpaI and inserted into the AscI and HpaI sites on the CMV driven mammalian expression vector carrying a neomycin selection marker. Similarly the hCG alpha DNA was digested with BamHI and NheI and inserted into the sites BamHI and NheI on the expression vector already containing the hCG beta polypeptide DNA.

The vector DNA was used to transform the DH5α strain of E. coli. Colonies were picked for amplification and, of the number which included the vector containing both hCG alpha and beta, twenty were selected for sequencing. All colonies selected for sequencing contained the correct sequences according to SEQ ID NO: 1 and SEQ ID NO: 3. Plasmid phCG A+B was selected for transfection (FIG. 1).

Example 2

Construction of the ST3 Expression Vector

The coding sequence of beta-galactoside alpha-2,3-sialyltransferase 4 (ST3, L23767, SEQ ID NO: 5) was amplified by PCR using the primer combination 2,3STfw and 2,3ST-rev.

2,3STfw (SEQ ID NO: 13)
5'-CCAGGATCCGCCACCATGTGTCCTGCAGGCTGGAAGC-3'

2,3STrev (SEQ ID NO: 14)
5'-TTTTTTTCTTAAGTCAGAAGGACGTGAGGTTCTTG-3'

The resulting amplified ST3 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST3#1 (FIG. 2) contained the correct sequence according to SEQ ID NO: 5 and was selected for transfection.

Example 3

Construction of the ST6 Expression Vector

The coding sequence of beta-galactosamide alpha-2,6-sialyltransferase 1 (ST6, NM_003032, SEQ ID NO: 7) was amplified by PCR using the primer combination 2,6STfw and 2,6STrev.

2,6STfw (SEQ ID NO: 15)
5'-CCAGGATCCGCCACCATGATTCACACCAACCTGAAG-3'

2,6STrev (SEQ ID NO: 16)
5'-TTTTTTTCTTAAGTTAGCAGTGAATGGTCCGG-3'

The resulting amplified ST6 DNA was digested with the restriction enzymes BamHI and AflII and inserted into the BamHI and AflII sites on the CMV driven mammalian expression vector carrying a hygromycin resistance marker. The vector was amplified as previously described and sequenced. Clone pST6#11 (FIG. 3) contained the correct sequence according to SEQ ID NO: 7 and was selected for transfection.

Example 4

Stable Expression of phCG A+B in PER.C6® Cells. Transfection Isolation and Screening of Clones PER.C6® clones producing hCG were generated by expressing both polypeptide chains of hCG from a single plasmid (see Example 1).

To obtain stable clones a liposome based transfection agent was used with the phCG A+B construct. Stable clones were selected in PER.C6® selection media supplemented with 10% FCS and containing G418. Three weeks after transfection G418 resistant clones grew out. A total of 389 clones were selected for isolation. The isolated clones were cultured in selection medium until 70-80% confluent. Supernatants were assayed for hCG protein content using an hCG selective ELISA and pharmacological activity at the hCG receptor in cloned cell line, using a cAMP accumulation assay. Clones (118) expressing functional protein were progressed for culture expansion to 24 well, 6 well and T80 flasks.

Studies to determine productivity and quality of the material from 47 clones were initiated in T80 flasks to generate sufficient material. Cells were cultured in supplemented media as previously described for 7 days and the supernatant harvested. Productivity was determined using the hCG selective ELISA. The isoelectric profile of the material was determined (using the method described in Example 6). The information from the IEF was used to select clones for metabolic clearance rate analysis. Clones with sufficient productivity and quality were selected for sialyltransferase engineering.

Example 5a

Level of Sialylation is Increased in Cells that over Express α2,3-sialyltransferase. Stable Expression of pST3 in hCG Expressing PER.C6® Cells; Transfection Isolation and Screening of Clones PER.C6® clones producing highly sialylated hCG were generated by expressing α2,3 sialyltransferase from separate plasmids (see Example 2) in PER.C6® cells already expressing both polypeptide chains of hCG (see Example 4). Clones produced from PER.C6® cells as set out in Example 4 were selected for their characteristics including productivity, good growth profile, production of functional protein, and produced hCG which included some sialylation.

Stable clones were generated as previously described in Example 4. Clones from the α2,3-sialyltransferase program were isolated, expanded and assayed. The final clone number for the α2,3-study was five. The α2,3-sialyltransferase clones were adapted to serum free media and suspension conditions.

As before clones were assayed using a hCG selective ELISA, functional response in an hCG receptor cell line, IEF (Example 6). They were also assessed for metabolic clearance rate (Example 9) and USP hCG Bioassay (Example 10). Results were compared to a commercially available recombinant hCG (OVITRELLE®, Serono) and the parental hCG PER.C6® cell lines. Representative samples are shown in the Examples and Figures.

In conclusion expression of hCG together with α2,3-sialyltransferase in PER.C6® cells results in increased levels of sialylated hCG compared to cells expressing hCG only.

Example 5b

Stable Expression of pST3 in hCG Expressing PER.C6® Cells—a Different Method

The alpha beta heterodimer produced above (Example 4) had a low level of sialylation resulting in a very basic IEF profile. As indicated above (Example 5a) expression of hCG together with α2,3-sialyltransferase in PER.C6® cells results in increased levels of sialylated hCG compared to cells expressing hCG only.

A double transfection of the hCG alpha and beta subunit genes together with the α2,3 sialyltransferase enzyme gene into PER.C6® cells in suspension cell culture format was performed. Cell lines were generated by co-transfecting the hCG vector (dual alpha/beta, Example 1) and the vector encoding α2,3-sialyltransferase (Example 2) under serum free conditions. Clones produced from PER.C6® cells were selected for their characteristics including productivity, good growth profile, production of functional protein, and produced hCG which included some sialylation. Clones were isolated, expanded and assayed.

As before clones were assayed using a hCG selective ELISA, functional response in an hCG receptor cell line, IEF (Example 6). They were also assessed for metabolic clearance rate (Example 9) and USP hCG Bioassay (Example 10). Results were compared to a commercially available recombinant hCG (OVITRELLE®, Serono) and the parental hCG PER.C6® cell lines. Representative samples are shown in the Examples and Figures (see Examples 6, 9, 10, FIGS. 4 and 5). The recombinant hCG produced by the clones (that is, recombinant hCG according to the invention) has significantly improved sialylation (i.e. on average more hCG isoforms with high numbers of sialic acids), compared to hCG expressed without α2,3- sialyltransferase and OVITRELLE® (see Examples 6 and 8, FIG. 4).

Figure 4:
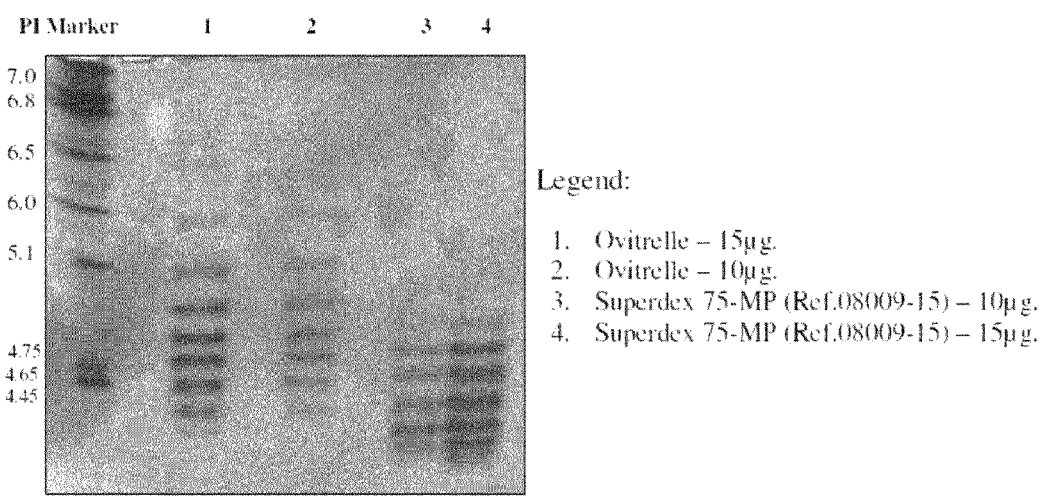
FIG. 4 shows the detection of rhCG Isoforms in human cell line derived recombinant hCG preparations according to the invention (track 3, 4) by IEF stained with Coomassie Blue, compared with preparations of the prior art (track 1, 2)

FIG. 4 are images showing gels showing the detection of rhCG Isoforms by IEF stained with Coomassie Blue in compositions according to the invention (Track 3, 10 µg, and Track 4, 15 µg) and the CHO derived composition of the prior art, OVITRELLE® (Track 1, OVITRELLE®, 10 µg, and Track 2, OVITRELLE®, 15 µg). The bands represent isoforms of hCG containing different numbers of sialic acid molecules. FIG. 4 indicates that human cell line derived recombinant hCGs engineered with α2,3-sialyltransferase (compositions according to the invention) have a more acidic profile than OVITRELLE®.

Example 6

Analysis of the Isoelectric Point pI of PER.C6® Produced hCG Isoforms by Isoelectric Focussing Electrophoresis is defined as the transport of charged molecules through a solvent by an electrical field. The mobility of a biological molecule through an electric field will depend on the field strength, net charge on the molecule, size and shape of the molecule, ionic strength and properties of the medium through which the molecules migrate.

Isoelectric focusing (IEF) is an electrophoretic technique for the separation of proteins based on their pI. The pI is the pH at which a protein has no net charge and will not migrate in an electric field. The sialic acid content of the hCG isoforms subtly alters the pI point for each isoform, which can be exploited using this technique to visualise the PER.C6® hCG isoforms from each clone.

The isoelectric points of the PER.C6® produced hCG isoforms in cell culture supernatants were analyzed using isoelectric focussing. Cell culture media from PER.C6® hCG clones were produced as described in Example 4, 5a and 5b.

PER.C6® hCG samples were separated on NOVEX® IEF Gels containing 5% polyacrylamide under native conditions on a pH 3.0-7.0 gradient in an ampholyte solution pH 3.0-7.0. Proteins were visualised using Coomassie Blue staining, using methods well known in the art.

FIG. 4 shows the detection of rhCG Isoforms by IEF stained with Coomassie Blue in compositions according to the invention (Track 3, 10 µg, and Track 4, 15 µg) and the CHO derived composition of the prior art, OVITRELLE® (Track 1, OVITRELLE®, 10 µg, and Track 2, OVITRELLE®, 15 µg). The bands represent isoforms of hCG containing different numbers of sialic acid molecules. Using this method clones producing hCG isoforms with a higher number of sialic acid molecules were identified. FIG. 4 indicates that human cell line derived recombinant hCGs engineered with α2,3-sialyltransferase have a more acidic profile than OVITRELLE®.

Example 7

Analysis of the Sialic Acid Linkages of PER.C6® hCG

Glycoconjugates were analyzed using a lectin based glycan differentiation method. With this method glycoproteins and glycoconjuagates bound to nitrocellulose can be characterized. Lectins selectively recognize a particular moiety, for example α2,3 linked sialic acid. The lectins applied are conjugated with the steroid hapten digoxigenin which enables immunological detection of the bound lectins.

Purified PER.C6® hCG from a parental clone (no additional sialyltransferase), and a α2,3-sialyltransferase engineered clone were separated using standard SDS-PAGE techniques. A commercially available recombinant hCG (OVITRELLE®, Serono) was used as a standard.

Sialic acid was analyzed using the DIG Glycan Differentiation Kit (Cat. No. 11 210 238 001, Roche) according to the manufacturer's instructions. Positive reactions with Sambucus nigra agglutinin (SNA) indicated terminally linked (2-6) sialic acid. Positive reactions with Maackia amurensis agglutinin II (MAA): indicated terminally linked (α2-3) sialic acid.

In summary the parental clone contained low levels of both α2,3- and α2,6-sialic acid. The clones engineered with α2,3-sialyltransferase contained high levels of α2,3-sialic acid linkages and low levels of α2,6-sialic acid linkages. The standard control Ovitrelle only contains α2,3-sialic acid linkages. This is consistent with what is known about recombinant proteins produced in Chinese Hamster ovary (CHO) cells (Kagawa et al, 1988, Takeuchi et al, 1988, Svensson et al., 1990).

In conclusion, engineering of PER.C6® hCG cells with α2,3-sialyltransferase successfully increased the number of sialic acid molecules conjugated to the recombinant hCG in the sample.

Examples 8A and 8B

Quantification of Total Sialic Acid

Sialic acid is a protein-bound carbohydrate considered to be a mono-saccharide and occurs in combination with other mono-saccharides like galactose, mannose, glucosamine, galactosamine and fucose. The total sialic acid on purified rhCG according to the invention was measured using a method based on the method of Stanton et. al. (J. Biochem. Biophys. Methods. 30 (1995), 37-48).

Example 8A

The total sialic acid content of PER.C6® recombinant hCG modified with α2,3-sialyltransferase (e.g. Example 5a, Example 5b) was measured and found to be greater than 15 mol/mol, [expressed in terms of a ratio of moles of sialic acid to moles of protein], for example greater than 18 mol/mol, for example 19.1 mol/mol. This can be compared to OVITRELLE® which has total sialic acid content of 17.6 mol/mol.

Example 8B

The total sialic acid content of PER.C6® recombinant hCG modified with α2,3-sialyltransferase 080019-19 (prepared by the methods of Example 5b above) was measured and found to be 20 mol/mol, [expressed in terms of a ratio of moles of sialic acid to moles of protein]. Again, this may be favourably compared with OVITRELLE® which has total sialic acid content of 17.6 mol/mol. This Example (080019-19) was tested to quantify the relative amounts of α2,3 and α2,6 sialic acid (Example 8C).

Example 8C

Quantification of Relative Amounts of α2,3 and α2,6 Sialic Acid

The relative percentage amounts of α2,3 and α2,6 sialic acid on purified rhCG [Example (080019-19), and two other Examples prepared by the methods of Example 5] were measured using known techniques —HPLC with Normal-phase (NP).

To quantify the alpha 2,3 and 2,6 sialic acid in O-link glycans the following analysis was performed. The O-linked glycans were cleaved from the hCG sample using an Orela Glycan Release Kit and separated on NP-HPLC. Samples of the extracted, pooled, glycans (extracted as above) were digested with different sialidases to determine the linkages. This Enzymatic degradation of glycans was performed using alpha 2-3,6,8 sialidase and alpha 2-3, sialidase. The enzymatic digested glycans were then re-separated on the NP column, and the O-Glycans were identified on the NP-HPLC using prepared standards. The relative percentages were calculated and are shown in the following table (SA=Sialic Acid).

| % SA | | | |
|---|---|---|---|
| 09PD84-006-3 | 09PD-84-04 | 080019-19 | Structure |
| 63 | 63 | 59 | α 2, 3 SA |
| 37 | 37 | 41 | α 2, 6 SA |

The relative percentages were found to be in the ranges 55%-65% (e.g. 59%) for α2,3 sialylation; and 35 to 45% (e.g. 41%) for α2,6 sialylation.

Example 8D

Quantification of Relative Amounts Mono, Di, Tri and Tetra Antennary Sialylated Structures The relative percentage amounts of mono, di, tri and tetra sialylated structures on glycans extracted from purified rhCG (the three samples used in Example 8C) were measured using known techniques.

Each sample of rhCG was immobilized (gel block), washed, reduced, alkylated and digested with PNGase F overnight. The N-glycans were then extracted and processed. N-glycans for NP-HPLC and WAX-HPLC analysis were labelled with the fluorophore 2AB as detailed in Royle et al.

Weak anion exchange (WAX) HPLC to separate the N-glycans by charge (Example 8C) was carried out as set out in Royle et al, with a Fetuin N-glycan standard as reference. Glycans were eluted according to the number of sialic acids they contained. All samples included mono (1S), di(2S), tri(3S) and tetra(4S) sialylated structures. The relative amounts of sialylated structures were found to be in the following ratios (1S:2S:4S:4S): 0.1-4%:35-45%:0.5-8%:0-1%.

A preferred example, 080019-19, included mono (1S), di(2S), tri(3S) and tetra(4S) sialylated structures. The relative amounts of sialylated structures were in the following ratios (1S:2S:4S:4S): 0.1-4%:35-45%:0.5-8%:0-1%.

Example 9

Determination of the Metabolic Clearance Rates of rhCG

Figure 5:
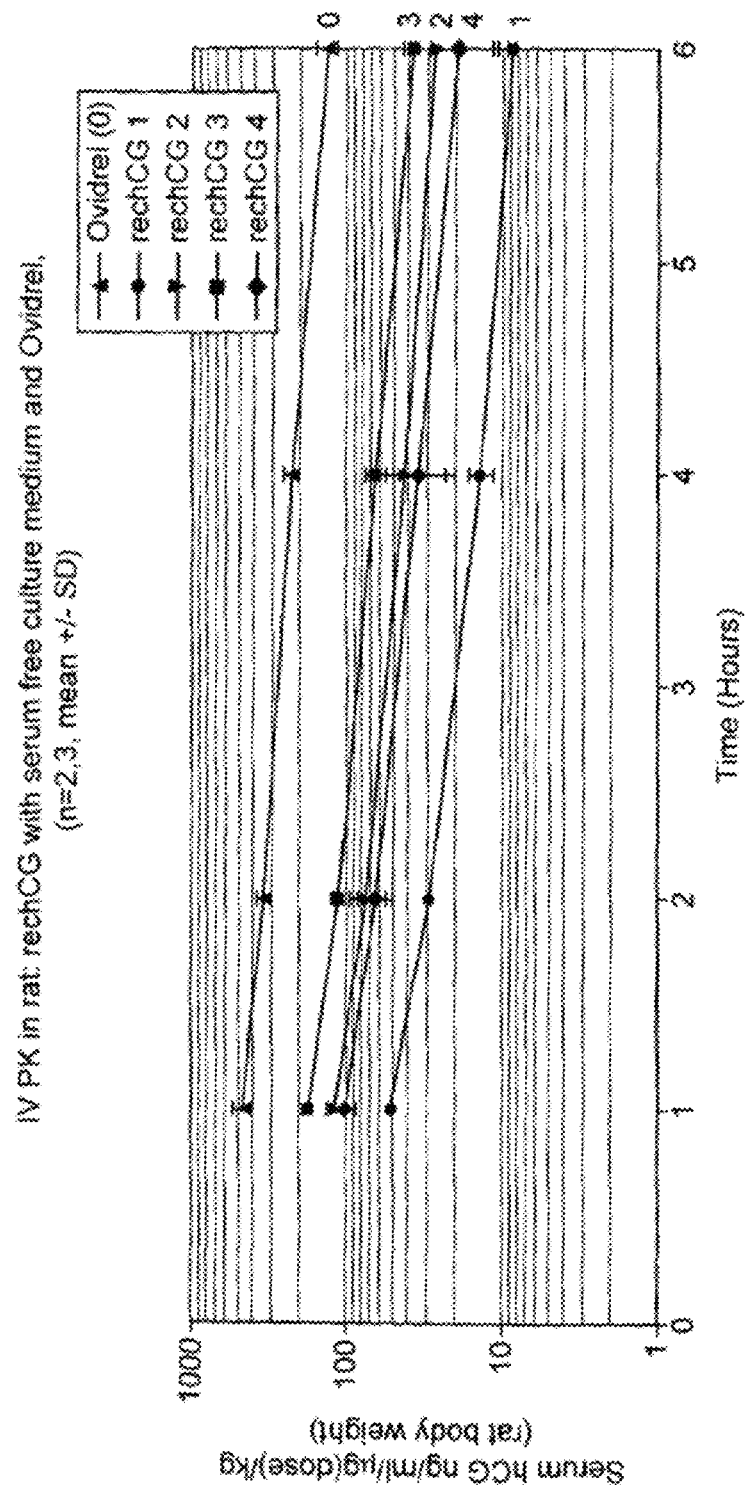
FIG. 5 shows metabolic clearance rates (MCRs) of α2,3-sialyltransferase engineered PER.C6® hCG samples.
Figure 6:
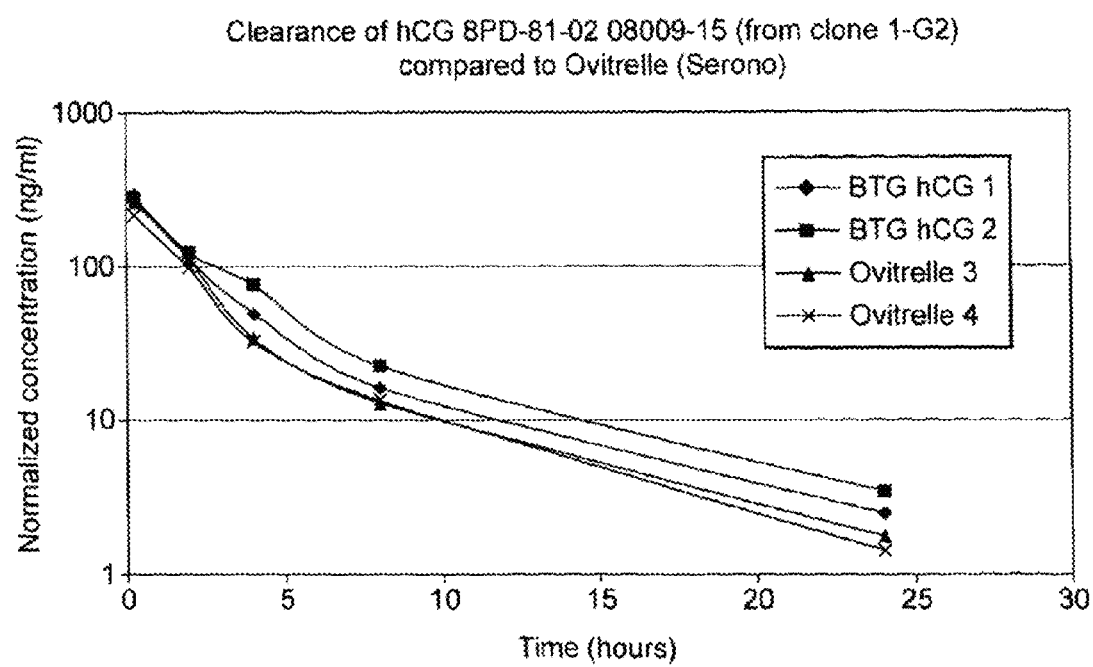
FIG. 6 shows long term MCRs of α2,3 sialyltransferase engineered PER.C6® rhCG samples.

To determine the metabolic clearance rate (MCR) of PER.C6® hCG samples engineered using α2,3-sialyltransferase (e.g. Example 5a, 5b), conscious female rats (3 animals per clone) were injected into the tail vein at time zero with a bolus of rhCG (1-10 µg/rat, based on ELISA quantification of samples, DRG EIA 1288). Blood samples (400 µl) were taken from the tip of the tail at 1, 2, 4, 8, 12, 24 and 32 hours after test sample injection. Serum was collected by centrifugation and assayed for hCG content by ELISA (DRG EIA 1288). The MCR of PER.C6® hCG samples engineered using α2,3-sialyltransferase showed that the half life was similar to the standard (FIG. 5). FIG. 6 shows that other hCG samples engineered using α2,3-sialyltransferase may have improved half life compared to the standard (FIG. 6).

FIG. 5 is a graph showing metabolic clearance rates of α2,3-sialyltransferase engineered PER.C6® cell produced rhCG samples. Samples were chosen for their sialic acid content based on their IEF profile. Female rats (3 animals per clone) were injected into the tail vein at time zero with a bolus of rhCG (1-10 µg/rat). Blood samples collected over time were assayed for hCG content by ELISA FIG. 6 is a graph showing long term clearance rates of α2,3-sialyltransferase engineered PER.C6® cell produced rhCG samples. Female rats (3 animals per clone) were injected into the tail vein at time zero with a bolus of rhCG (1-10 µg/rat). Blood samples collected over time were assayed for hCG content by ELISA.

Example 10 hCG Bioassay According to USP

A hCG Bioassay was carried out, to assay the hCG specific activity. The activity was measured according to USP (USP Monographs: Chorionic Gonadotropin, USPC Official Aug. 1, 2009-Nov. 30, 2009), using OVITRELLE® as a standard. OVITRELLE® has a biological activity of 26,000 IU/mg (Curr Med Res Opin. 2005 December; 21(12): 1969-76). The acceptance limit was >21,000 IU hCG/mg. The biological activity for a sample of human cell line derived hCG recombinant hCG engineered with α2,3-sialyltransferase (having sialic acid content 19.1 mol/mol—see Example 8) was 27,477 IU hCG/mg.

Example 11

Production and Purification Overview

A procedure was developed to produce recombinant hCG in PER.C6® cells that were cultured in suspension in serum free medium. The procedure is described below and was applied to several hCG-producing PER.C6® cell lines.

Recombinant hCG from an α2,3- clone was purified using a using a modification of the method described by Lowry et al. (1976).

For the production of PER.C6®-cell produced hCG, the cell lines were adapted to a serum-free medium, i.e., EX-CELL® 525 (JRH Biosciences). The cells were first cultured to form a 70%-90% confluent monolayer in a T80 culture flask. On passage the cells were re-suspended in the serum free medium, EX-CELL® 525+4 mM L-Glutamine, to a cell density of $0.3 \times 10^6$ cells/ml. A 25 ml cell suspension was put in a 250 ml shaker flask and shaken at 100 rpm at 37° C. at 5% $CO_2$. After reaching a cell density of $>1 \times 10^6$ cells/ml, the cells were sub-cultured to a cell density of 0.2 or $0.3 \times 10^6$ cells/ml and further cultured in shaker flasks at 37° C., 5% $CO_2$ and 100 rpm.

For the production of hCG, the cells were transferred to a serum-free production medium, i.e., VPRO (JRH Biosciences), which supports the growth of PER.C6® cells to very high cell densities (usually $>10^7$ cells/ml in a batch culture). The cells were first cultured to $>1 \times 10^6$ cells/ml in EX-CELL® 525, then spun down for 5 min at 1000 rpm and subsequently suspended in VPRO medium+6 mM L-glutamine to a density of $1 \times 10^6$ cells/ml. The cells were then cultured in a shaker flask for 7-10 days at 37° C., 5% CO2 and 100 rpm. During this period, the cells grew to a density of $>10^7$ cells/ml. The culture medium was harvested after the cell viability started to decline. The cells were spun down for 5 min at 1000 rpm and the supernatant was used for the quantification and purification of hCG. The concentration of hCG was determined using ELISA (DRG EIA 1288).

Thereafter, purification of hCG was carried out using a modification of the method described by Lowry et al. (1976). This was achieved by chromatography on DEAE cellulose, gel filtration on SEPHADEX® G100, adsorption chromatography on hydroxyapatite, and preparative polyacrylamide electrophoresis.

During all chromatographic procedures, the presence of immunoreactive recombinant hCG was confirmed by RIA (DRG EIA 1288) and IEF (Example 6).

Example 12

PEGylation

In an example of the present invention, poly (ethylene glycol) is (e.g. covalently) bound through amino acid residues of hCG (or agonist variant thereof). Preferably the poly (ethylene glycol) is bound to the N-terminus of the hCG. A number of activated poly (ethylene glycol) s having a number of different functional groups, linkers, configurations, and molecular weights are known to one skilled in the art. These may be used to synthesise PEG-hCG conjugates or PEG-hCG agonist variant conjugates, by methods which are known in the art (see e.g. Roberts M. J. et al., Adv. Drug Del. Rev. 54: 459-476, 2002), Harris J. M. et al., Drug Delivery Sytems 40: 538-551, 2001).

A substantially homogeneous preparation of N-terminally pegylated hGG was synthesised using a methoxy-PEG-Hydrazine (20 kD). Methoxy-PEG-Hydrazine (20 kD) are widely available and their uses are well known in the art. A transamination reaction was used to remove the amine group at the N-terminus of the human derived recombinant hCG, to leave an aldehyde in this position. A chemical reaction between the aldehyde group and the methoxy-PEG-Hydrazine (20 kD) leads to PEGylation of the hCG at the N-terminus. The PEGylated hCG product was purified from the reaction mixture to >95% (SEC analysis) using a single ion exchange chromatography step, by methods known in the art.

1 mg/mL of purified rhCG (produced in house by the method of Example 5b and purified according to the method of Example 11) in 20 mM ammonium acetate, 150 mM NaCl (pH 8) was concentrated to 3 mg/mL, and conditioned to 50 mM Sodium acetate, 150 mM NaCl pH 5.5 buffer by 10KD-ultracentrifugal device (VIVASPIN® 20) at 4,000 rpm, 8° C.

Transamination: The concentrated hCG was incubated at room-temperature for 4 hours in a solution containing 2M-sodium acetate, 0.4M acetic acid, 0.1M sodium glyoxylate and 5 mM $CuSO_4$ (ph 5.5). The reaction was then stopped by adding EDTA to a final concentration of 20 mM. A 10KD-ultracentrifugal device was used to remove the undesirable transamination-components and the buffer exchanged to 50 mM sodium phosphate, 150 mM NaCl (pH 7.5).

PEGylation: An m-PEG-Hydrazine stock solution of 10 mM was prepared by dissolving lyophilized powder (NOF) in 1 mM HCl. A sodium cyanoborohydride stock solution of 200 mM was prepared by dissolving lyophilized powder (Fluka) in water.

Figure 7:
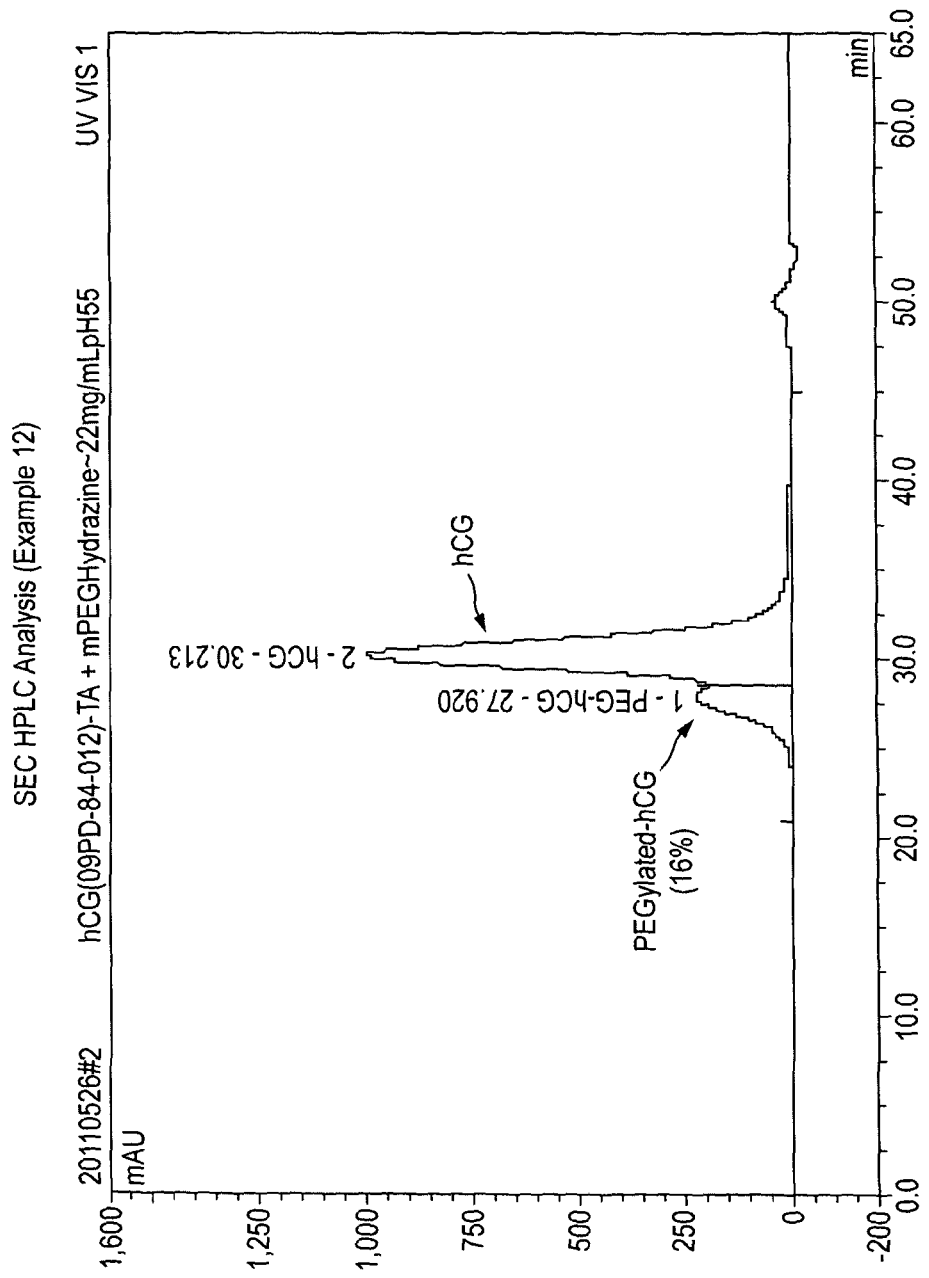
FIG. 7 shows the SEC HPLC analysis of the PEGylated hCG of the invention produced by the method of Example 12.

An 11-fold molar quantity of m-PEG-Hydrazine from the 10 mM stock solution was added to a vial containing transaminated-rhCG (3 mg/mL) while stirring. Immediately afterwards 75-folds molar of sodium cyanoborohydride was added from the stock solution, as a reducing agent. The reaction mixture was stirred at room-temperature for 24 hours and the extent of hCG modification by PEG (PEGylation) was monitored by size-exclusion chromatography (SEC) HPLC column; SUPERDEX®-75 (GE healthcare). After 24 hours, the reaction was stopped and diluted 1:1 to 1 mg/mL with 400 mM glycine, 50 mM sodium phosphate, 150 mM NaCl pH 6.7 buffer and final pH adjustment was carried-out with 1M HCl. The reaction mixture was 0.2 μm filtered, divided to aliquots and stored at 4° C. The SEC HPLC analysis is shown in FIG. 7.

It can be seen from the HPLC analysis (FIG. 7) that the method provided PEGylated hCG. About 16% of the hCG molecules were PEGylated. It is believed that the relatively low yield of this reaction was because about 80%-90% of the humanized proteins have acetyl-residues on their N-terminal, which meant that the yield of the hCG transamination step was relatively low.

Example 12A

PEGylation Using 2-Branched m-PEG-Aldehyde (20 Kd)

The functional group of m-PEG-Aldehyde mainly interacts with the N-terminal at pH 5.5. Experiments carried out with a linear m-PEG-Aldehyde yield PEGylated-hCG with about 6 to 7 PEG-strands rather than the expected 2-strands. This implies that m-PEG-Aldehyde interacts with other amino-acids, such as Histidine (hCG has 4 Histidine residues).

The present inventors found that the use of a 2-Branched m-PEG-Aldehyde reduced or prevented unwanted PEGylations (steric hindrance suppresses access to sites other than the N-terminus) and increased the yield of a product with only N-terminal PEGylation. The procedure that was carried-out is shown in Scheme 1 and is as follows.

A 10-fold molar quantity of the 2-Branched m-PEG-Aldehyde from the 10 mM stock solution was added to a vial containing rhCG (3 mg/mL), and stirred. Immediately afterwards a 75-folds molar quantity of sodium cyanoborohydride, as reducing agent, was added from the stock solution. The reaction mixture was stirred at room-temperature for 24 hours and the extent of modification of hCG by the PEG (PEGylation) was monitored by size-exclusion chromatography (SEC) HPLC column; SUPERDEX®-200 (GE healthcare). After 24 hours the reaction was stopped and diluted 1:1 to 1 mg/mL with 400 mM glycine, 50 mM sodium phosphate, 150 mM NaCl (pH 6.7 buffer). The final pH adjustment was carried-out with 1M HCl. The reaction mixture was 0.2 µm filtered, divided to aliquots and stored at 4° C.

Figure 8A:
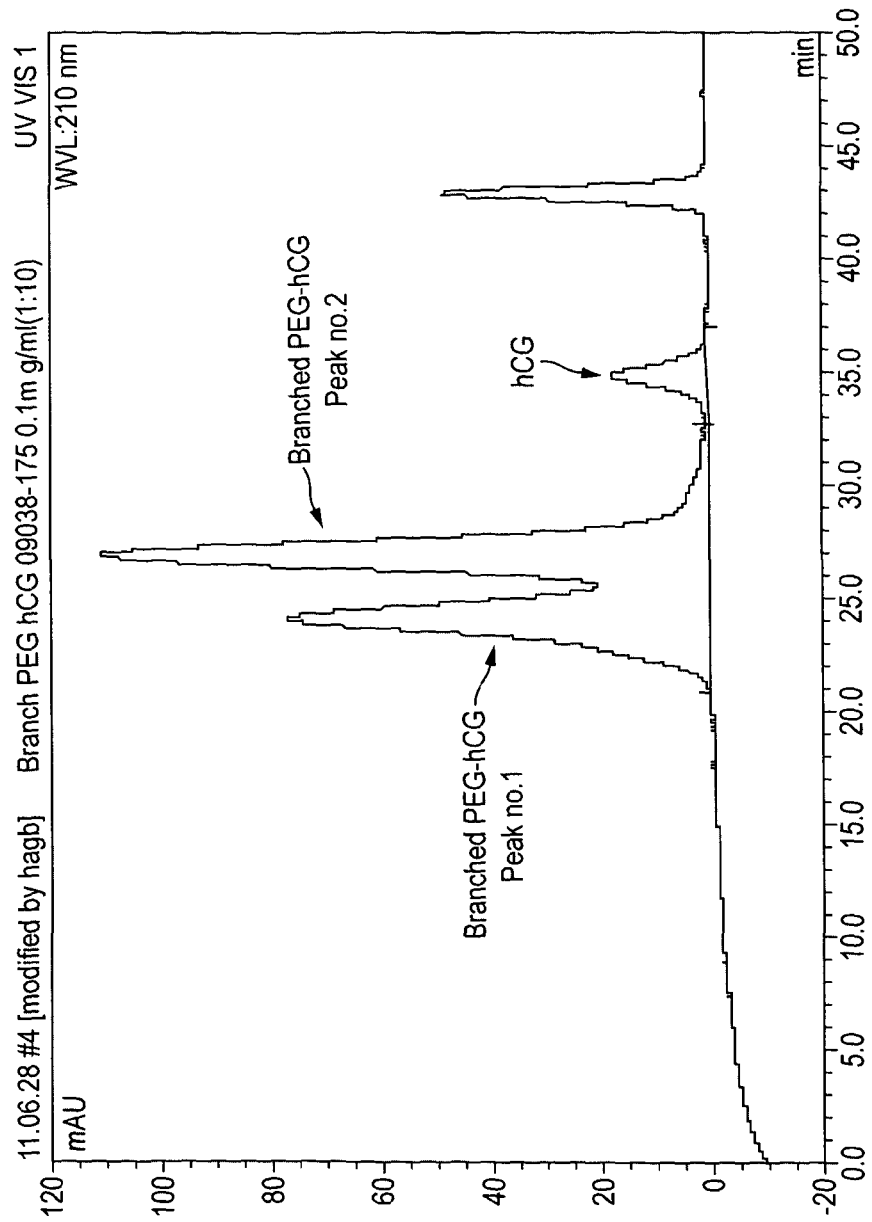
FIGS. 8A and 8B show the SEC HPLC analysis of the PEGylated hCG products of the invention produced by the methods of Examples 12A and 12B.

The SEC (Superdex SUPERDEX®-200 10/300 mm GL) HPLC Analysis is shown in FIG. 8A. As presented in FIG. 8-A, two populations of PEGylated-hCG were observed. The first eluted peak (no.1) was the higher molecular weight PEG-strands and the second eluted peak (no.2) was the lower molecular weight PEG-strands. 94% of the hCG

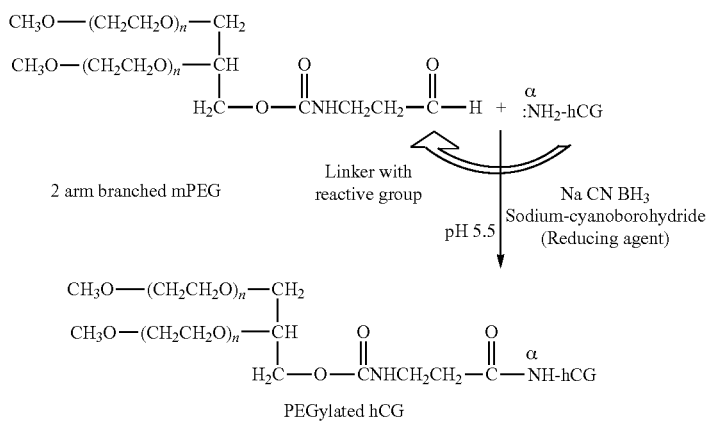

[In schemes 1, 2 and 3 herein $CH_3-(CH_2CH_2O)_n$ is the common nomenclature representing mPEG. The integers n and m in schemes 1, 2 and 3 do not have the same meaning as those integers in the present claims.

1 mg/mL of purified rhCG (produced in house by the method of Example 5b and purified according to the method of Example 11) in 20 mM ammonium acetate, 150 mM NaCl pH 8 was concentrated to 3 mg/mL and conditioned to 50 mM ammonium acetate, 150 mM NaCl (pH 5.5) buffer by 10KD-ultracentrifugal device (VIVASPIN® 20) at 4,000 rpm, 8° C.

A 2-Branched m-PEG-Aldehyde (40 KD) stock solution of 10 mM was prepared by dissolving lyophilized powder (NOF) in 1 mM HCL. A Sodium Cyanoborohydride stock solution of 200 mM was prepared by dissolving lyophilized powder (Fluke) in water.

molecules were PEGylated, representing a considerable increase in yield over Example 12. The determination of PEG-strand number in each population was impossible under the SEC-conditions used, because the remaining free 2-Branched m-PEG-Aldehyde elutes at the same RT (retention time) as the PEGylated-hCG. The product Branched-PEGylated hCG was tested for its activity in a bioassay (Example 13).

It will be appreciated that the use of a higher branched m-PEG reagent (for example a 4-Branched m-PEG-Aldehyde such as that represented below) is more likely to produce a single population of PEG-hCG with lower PEG-strands (Peak no.2 on FIG. 1-B), because a 4 branched m-PEG-Aldehyde will further suppress access to other sites besides the N-terminus.

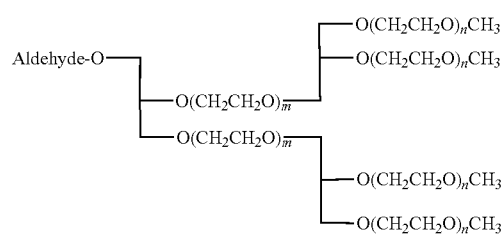
Total Mw 40kDa: 5k × 2.7.5k × 4
60kDa: 5k × 2.12.5k × 4
80kDa: 5k × 2.17.5k × 4
A suitable scheme for preparing a 4-arm branched mPEG Aldehyde by a similar method to that shown in scheme 1 above is shown in scheme 2
Scheme 2: hCG PEGylation with 4 arm branched mPEG Aldehyde:
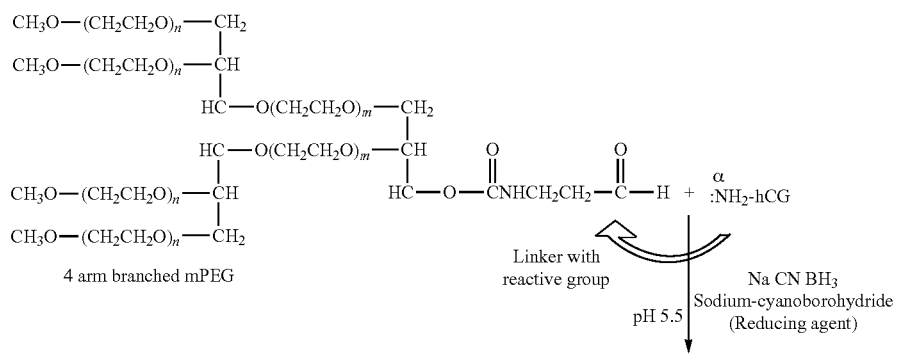
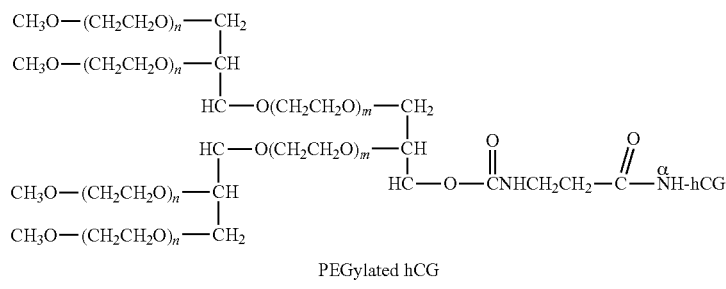
PEGylated hCG

Example 12B

The rhCG (produced in house by the method of Example 5b and purified according to the method of Example 11) was modified with a linear m-PEG-Aldehyde (10 KD), using the method of Example 12A. The procedure that was carried-out is shown in Scheme 3 and is as follows:

Scheme 3: hCG PEGylation with linear mPEG Aldehyde:

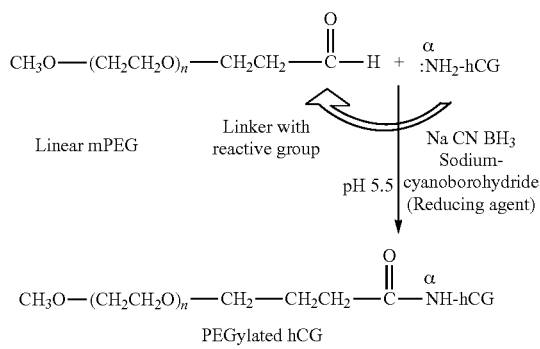

Figure 8B:
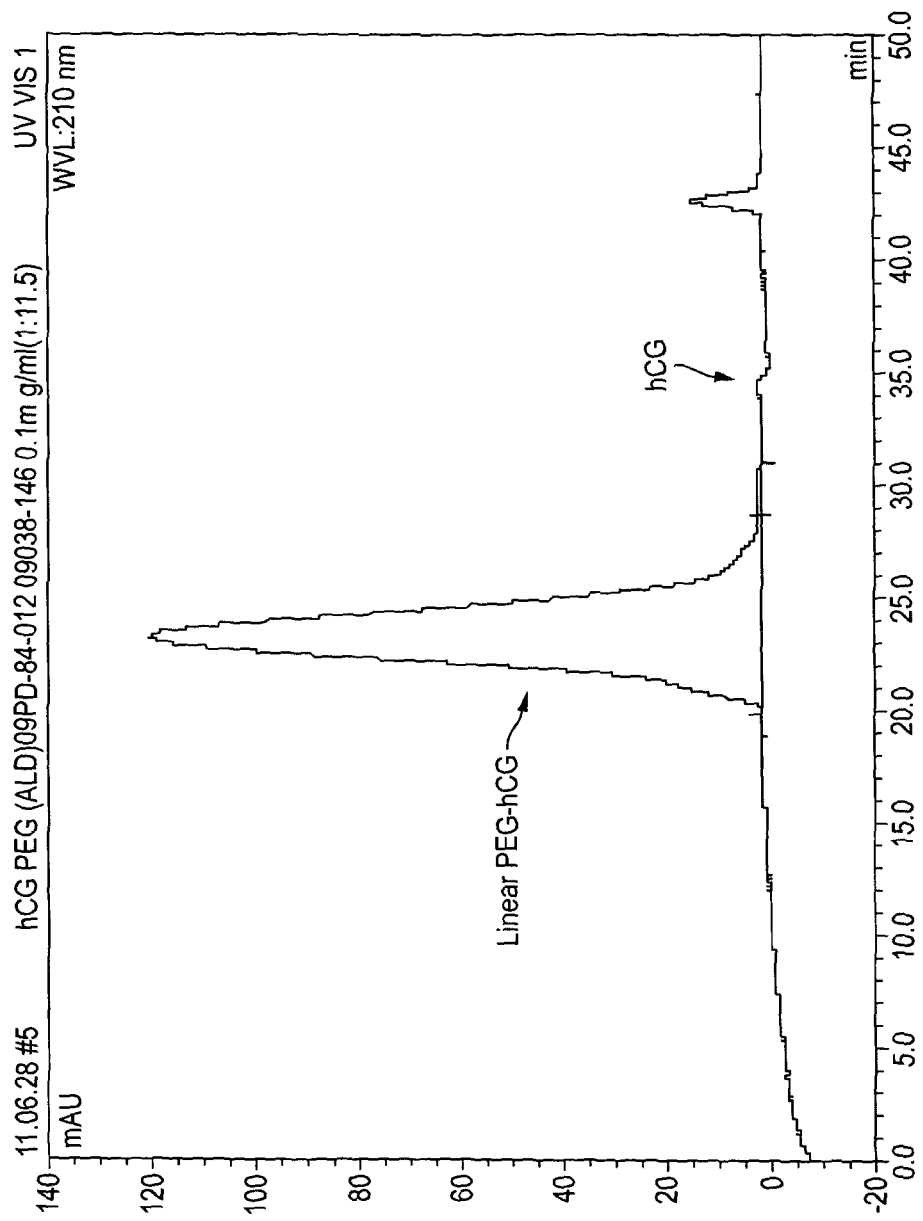

The SEC-HPLC analysis of the product linear-PEGylated hCG is presented in FIG. 8-B. This linear-PEGylated hCG was also tested for its activity in a bioassay (Example 13).

Example 13

Activated-PEG hCG Bioassay

A recombinant hCG was produced by the method of Example 5b and purified according to the method of Example 11. 21 rats were allocated into 3 groups (7 rats per group), and each rat was injected three times, on three separate days (each injection at different day), with one of the following doses of the recombinant hCG (1 group=1 dose): 4.3 ng (rats in Group A), 8.6 ng (rats in Group B); and 17.1 ng (rats in Group C). After 5 days the rats were sacrificed and the uterus weighed for potency determination, according to a known and routine Bioassay.

A rat which has been injected with 3 daily doses totalling 4.3 ng of the recombinant hCG has average Uterus weight of 30-40 mg after 5 days. A rat which has been injected with 3 daily doses totalling 8.6 ng rhCG has average Uterus weight of 60-70 mg after 5 days. A rat which has been injected with 3 daily doses of 17.1 ng rhCG has average Uterus weight of 110-120 mg after 5 days (see Table below).

The inventors tested the products of the invention for potential to provide a long acting formulation which would allow a single weekly dose.

The present inventors used the same Bioassay to measure the uterus weight after 5 days of rats treated with:

(i) a single injection of Recombinant hCG produced in house by the method of Example 5b and purified according to the method of Example 11, which was administered at ten times the concentration of the highest of the three daily injection doses, that is at ten times the concentration (170 ng);

(ii) a single injection of Branched-PEGylated recombinant hCG of the invention produced by the method of Example 12A which was administered at ten times the concentration of the highest of the three daily injection doses, that is at ten times the concentration (170 ng); and (iii) a single injection of Linear-PEGylated recombinant hCG of the invention produced by the method of Example 12 which was administered at ten times the concentration of the highest of the three daily injection doses, that is at ten times the concentration (170 ng).

The results are shown in the following Table.

It can be seen that the branched PEG-rhCG Bioassay example (Column 5 of the Table) demonstrates that a single injection of the branched PEGylated rhCG of the invention provides an average uterus weight (mg) of 134.11, roughly equivalent to 3 single injections of the highest dose of 17.1 ng rhCG. This strongly indicates that a "one-week sustained release" formulation would be viable using the PEGylated hCG of the invention. This ability to provide a one week formulation of recombinant hCG represents a significant advantage over the known hCG formulations.

| | Average Uterus Weight (mg) | | | | |
|---|---|---|---|---|---|
| Group | rhCG QS-MP 09PD-84-012 3 injections of 4.3 ng (Group A), 8.6 ng (Group B) and 17.1 ng (Group C) | rhCG QS-MP 09PD-84-012 X 10 Conc. 1 Injection (170 ng) Group (i) | Linear PEG-rhCG QS-MP 09PD-84-012 X 10 Conc. 1 Injection (170 ng) Group (iii) | Branch PEG-rhCG QS-MP 09PD-84-012 X 10 Conc. 1 Injection (170 ng) Group (ii) | Buffer |
| A | 38.81 | | | | |
| B | 57.28 | | | | |
| C | 117.23 | 64.05 | 35.22 | 134.11 | 41.9 | rhCG = recombinant hCG

REFERENCES

Andersen C Y, Westergaard L G, and van Wely M. (2004). FSH isoform composition of commercial gonadotrophin preparations: a neglected aspect? Reprod Biomed Online. 9(2), 231-236.

Bassett R M, and Driebergen R. (2005). Continued improvements in the quality and consistency of follitropin alfa, recombinant human FSH. Reprod Biomed Online. 10(2), 169-177.

D'Antonio M., Borrelli F., Datola A., Bucci R., Mascia M., Polletta P., Piscitelli D., and Papoian R. (1999) Biological characterization of recombinant human follicle stimulating hormone isoforms. Human Reproduction 14, 1160-1167

Fiddes, J. C. and Goodman, H. M. (1979) Isolation, cloning and sequence analysis of the cDNA for the alpha-subunit of human chorionic gonadotropin. Nature, 281, 351-356.

Fiddes, J. C. and Goodman, H. M. (1980) The cDNA for the beta-subunit of human chorionic gonadotropin suggests evolution of a gene by readthrough into the 3'-untranslated region. Nature, 286, 684-387.

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol. Chem. 263(33), 17508-17515.

Lowry O H, Rosebrough N J, Farr A L, Randall R J. (1951) Protein measurement with the Folin phenol reagent. J Biol Chem. 193(1), 265-75.

Lowry, P J, McLean, C, Jones R L and Satgunasingam N. (1976) Purification of anterior pituitary and hypothalamic hormones Clin Pathol Suppl (Assoc Clin Pathol). 7, 16-21.

Royle L, Radcliffe C M, Dwek R A and Rudd P M (2006) Methods in Molecular Biology, ed I Brockhausen-Schutzbach (Humana Press), 347: Glycobiology protocols, 125-144.

Steelman S L, and Pohley F M. (1953) Assay of the follicle stimulating hormone based on the augmentation with human chorionic gonadotropin. Endocrinology. 53(6), 604-616.

Svensson E C, Soreghan B, and Paulson J C. (1990) Organization of the beta-galactoside alpha 2,6-sialyltransferase gene. Evidence for the transcriptional regulation of terminal glycosylation. J Biol Chem. 265(34):20863-20868.

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Ulloa-Aguirre A, Midgley A R Jr, Beitins I Z, and Padmanabhan V, (1995). Follicle-stimulating isohormones: characterization and physiological relevance. Endocr Rev. 16(6), 765-787.

Ulloa-Aguirre A, Timossi C, Barrios-de-Tomasi J, Maldonado A, and Nayudu P. (2003). Impact of carbohydrate heterogeneity in function of follicle-stimulating hormone: studies derived from in vitro and in vivo models. Biol Reprod. 69(2), 379-389.

```
Human chorionic gonadotropin alpha polypeptide
Accession number AH007338
Nucleotide sequence of hCG alpha
                                                        SEQ ID 1
    1 ATGGATTACT ACAGAAAATA TGCAGCTATC TTTCTGGTCA CATTGTCGGT GTTTCTGCAT

61 GTTCTCCATT CCGCTCCTGA TGTGCAGGAT TGCCCAGAAT GCACGCTACA GGAAAACCCA

121 TTCTTCTCCC AGCCGGGTGC CCCAATACTT CAGTGCATGG GCTGCTGCTT CTCTAGAGCA

181 TATCCCACTC CACTAAGGTC CAAGAAGACG ATGTTGGTCC AAAAGAACGT CACCTCAGAG

241 TCCACTTGCT GTGTAGCTAA ATCATATAAC AGGGTCACAG TAATGGGGGG TTTCAAAGTG

301 GAGAACCACA CGGCGTGCCA CTGCAGTACT TGTTATTATC ACAAATCTTA A

Protein sequence of hCG alpha
    1 MDYYRKYAAI FLVTLSVFLH VLHSAPDVQD CPECTLQENP FFSQPGAPIL QCMGCCFSRA

61 YPTPLRSKKT MLVQKNVTSE STCCVAKSYN RVTVMGGFKV ENHTACHCST CYYHKS

Human Chorionic Gonadotrophin beta polypeptide
Accession number NP_000728
Nucleotide sequence of hCG beta
Nucleotide sequence
                                                        SEQ ID 2
    1 ATGGAGATGT TCCAGGGGCT GCTGCTGTTG CTGCTGCTGA GCATGGGCGG GACATGGGCA

61 TCCAAGGAGC CGCTTCGGCC ACGGTGCCGC CCCATCAATG CCACCCTGGC TGTGGAGAAG

121 GAGGGCTGCC CCGTGTGCAT CACCGTCAAC ACCACCATCT GTGCCGGCTA CTGCCCCACC

181 ATGACCCGCG TGCTGCAGGG GGTCCTGCCG GCCCTGCCTC AGGTGGTGTG CAACTACCGC

241 GATGTGCGCT TCGAGTCCAT CCGGCTCCCT GGCTGCCCGC GCGGCGTGAA CCCCGTGGTC

301 TCCTACGCCG TGGCTCTCAG CTGTCAATGT GCACTCTGCC GCCGCAGCAC CACTGACTGC

361 GGGGGTCCCA AGGACCACCC CTTGACCTGT GATGACCCCC GCTTCCAGGA CTCCTCTTCC

421 TCAAAGGCCC CTCCCCCCAG CCTTCCAAGT CCATCCCGAC TCCCGGGGCC CTCGGACACC

481 CCGATCCTCC CACAATAA

Protein sequence of hCG beta
    1 MEMFQGLLLL LLLSMGGTWA SKEPLRPRCR PINATLAVEK EGCPVCITVN TTICAGYCPT

61 MTRVLQGVLP ALPQVVCNYR DVRFESIRLP GCPRGVNPVV SYAVALSCQC ALCRRSTTDC

121 GGPKDHPLTC DDPRFQDSSS SKAPPPSLPS PSRLPGPSDT PILPQ
```

Beta-galactoside alpha-2,3-sialyltransferase 4
Accession Number L23767
Nucleotide sequence of ST3GAL4

SEQ ID 3
```
  1 ATGTGTCCTG CAGGCTGGAA GCTCCTGGCC ATGTTGGCTC TGGTCCTGGT CGTCATGGTG

61 TGGTATTCCA TCTCCCGGGA AGACAGGTAC ATCGAGCTTT TTTATTTTCC CATCCCAGAG

121 AAGAAGGAGC CGTGCCTCCA GGGTGAGGCA GAGAGCAAGG CCTCTAAGCT CTTTGGCAAC

181 TACTCCCGGG ATCAGCCCAT CTTCCTGCGG CTTGAGGATT ATTTCTGGGT CAAGACGCCA

241 TCTGCTTACG AGCTGCCCTA TGGGACCAAG GGGAGTGAGG ATCTGCTCCT CCGGGTGCTA

301 GCCATCACCA GCTCCTCCAT CCCCAAGAAC ATCCAGAGCC TCAGGTGCCG CCGCTGTGTG

361 GTCGTGGGGA ACGGGCACCG GCTGCGGAAC AGCTCACTGG GAGATGCCAT CAACAAGTAC

421 GATGTGGTCA TCAGATTGAA CAATGCCCCA GTGGCTGGCT ATGAGGGTGA CGTGGGCTCC

481 AAGACCACCA TGCGTCTCTT CTACCCTGAA TCTGCCCACT TCGACCCCAA AGTAGAAAAC

541 AACCCAGACA CACTCCTCGT CCTGGTAGCT TTCAAGGCAA TGGACTTCCA CTGGATTGAG

601 ACCATCCTGA GTGATAAGAA GCGGGTGCGA AAGGGTTTCT GGAAACAGCC TCCCCTCATC

661 TGGGATGTCA ATCCTAAACA GATTCGGATT CTCAACCCCT TCTTCATGGA GATTGCAGCT

721 GACAAACTGC TGAGCCTGCC AATGCAACAG CCACGGAAGA TTAAGCAGAA GCCCACCACG

781 GGCCTGTTGG CCATCACGCT GGCCCTCCAC CTCTGTGACT TGGTGCACAT TGCCGGCTTT

841 GGCTACCCAG ACGCCTACAA CAAGAAGCAG ACCATTCACT ACTATGAGCA GATCACGCTC

901 AAGTCCATGG CGGGGTCAGG CCATAATGTC TCCCAAGAGG CCCTGGCCAT TAAGCGGATG

961 CTGGAGATGG GAGCTATCAA GAACCTCACG TCCTTCTGA
```

Protein Sequence of ST3GAL4
```
  1 MCPAGWKLLA MLALVLVVMV WYSISREDRY IELFYFPIPE KKEPCLQGEA ESKASKLFGN

61 YSRDQPIFLR LEDYFWVKTP SAYELPYGTK GSEDLLLRVL AITSSSIPKN IQSLRCRRCV

121 VVGNGHRLRN SSLGDAINKY DVVIRLNNAP VAGYEGDVGS KTTMRLFYPE SAHFDPKVEN

181 NPDTLLVLVA FKAMDFHWIE TILSDKKRVR KGFWKQPPLI WDVNPKQIRI LNPFFMEIAA

241 DKLLSLPMQQ PRKIKQKPTT GLLAITLALH LCDLVHIAGF GYPDAYNKKQ TIHYYEQITL

301 KSMAGSGHNV SQEALAIKRM LEMGAIKNLT SF
```

Beta-galactosamide alpha-2,6-sialyltransferase 1
Accession number NM_003032
Nucleotide sequence of ST6GAL1

SEQ ID 4
```
  1 ATGATTCACA CCAACCTGAA GAAAAAGTTC AGCTGCTGCG TCCTGGTCTT TCTTCTGTTT

61 GCAGTCATCT GTGTGTGGAA GGAAAAGAAG AAAGGGAGTT ACTATGATTC CTTTAAATTG

121 CAAACCAAGG AATTCCAGGT GTTAAAGAGT CTGGGGAAAT TGGCCATGGG GTCTGATTCC

181 CAGTCTGTAT CCTCAAGCAG CACCCAGGAC CCCCACAGGG GCCGCCAGAC CCTCGGCAGT

241 CTCAGAGGCC TAGCCAAGGC CAAACCAGAG GCCTCCTTCC AGGTGTGGAA CAAGGACAGC

301 TCTTCCAAAA ACCTTATCCC TAGGCTGCAA AAGATCTGGA AGAATTACCT AAGCATGAAC

361 AAGTACAAAG TGTCCTACAA GGGGCCAGGA CCAGGCATCA AGTTCAGTGC AGAGGCCCTG

421 CGCTGCCACC TCCGGGACCA TGTGAATGTA TCCATGGTAG AGGTCACAGA TTTTCCCTTC

481 AATACCTCTG AATGGGAGGG TTATCTGCCC AAGGAGAGCA TTAGGACCAA GGCTGGGCCT

541 TGGGGCAGGT GTGCTGTTGT GTCGTCAGCG GGATCTCTGA AGTCCTCCCA ACTAGGCAGA

601 GAAATCGATG ATCATGACGC AGTCCTGAGG TTTAATGGGG CACCCACAGC CAACTTCCAA

661 CAAGATGTGG GCACAAAAAC TACCATTCGC CTGATGAACT CTCAGTTGGT TACCACAGAG

721 AAGCGCTTCC TCAAAGACAG TTTGTACAAT GAAGGAATCC TAATTGTATG GGACCCATCT
```

```
 781 GTATACCACT CAGATATCCC AAAGTGGTAC CAGAATCCGG ATTATAATTT CTTTAACAAC

841 TACAAGACTT ATCGTAAGCT GCACCCCAAT CAGCCCTTTT ACATCCTCAA GCCCAGATG

901 CCTTGGGAGC TATGGGACAT TCTTCAAGAA ATCTCCCCAG AAGAGATTCA GCCAAACCCC

961 CCATCCTCTG GGATGCTTGG TATCATCATC ATGATGACGC TGTGTGACCA GGTGGATATT

1021 TATGAGTTCC TCCCATCCAA GCGCAAGACT GACGTGTGCT ACTACTACCA GAAGTTCTTC

1081 GATAGTGCCT GCACGATGGG TGCCTACCAC CCGCTGCTCT ATGAGAAGAA TTTGGTGAAG

1141 CATCTCAACC AGGGCACAGA TGAGGACATC TACCTGCTTG GAAAAGCCAC ACTGCCTGGC

1201 TTCCGGACCA TTCACTGCTA A

0p-
Protein Sequence of ST6GAL1
   1 MIHTNLKKKF SCCVLVFLLF AVICVWKEKK KGSYYDSFKL QTKEFQVLKS LGKLAMGSDS

61 QSVSSSSTQD PHRGRQTLGS LRGLAKAKPE ASFQVWNKDS SSKNLIPRLQ KIWKNYLSMN

121 KYKVSYKGPG PGIKFSAEAL RCHLRDHVNV SMVEVTDFPF NTSEWEGYLP KESIRTKAGP

181 WGRCAVVSSA GSLKSSQLGR EIDDHDAVLR FNGAPTANFQ QDVGTKTTIR LMNSQLVTTE

241 KRFLKDSLYN EGILIVWDPS VYHSDIPKWY QNPDYNFFNN YKTYRKLHPN QPFYILKPQM

301 PWELWDILQE ISPEEIQPNP PSSGMLGIII MMTLCDQVDI YEFLPSKRKT DVCYYYQKFF

361 DSACTMGAYH PLLYEKNLVK HLNQGTDEDI YLLGKATLPG FRTIHC
```

---

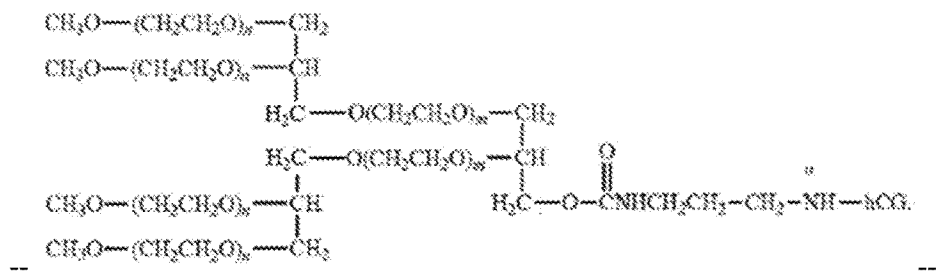

The invention claimed is:

1. A polyethylene glycol modified hCG of the following formula:

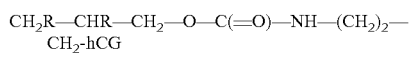
$$CH_2R—CHR—CH_2—O—C(=O)—NH—(CH_2)_2—CH_2\text{-hCG}$$

wherein each R is a polyethylene glycol (PEG) or a methoxypoly (ethylene glycol) (mPEG).

2. A polyethylene glycol modified hCG of the following formula:

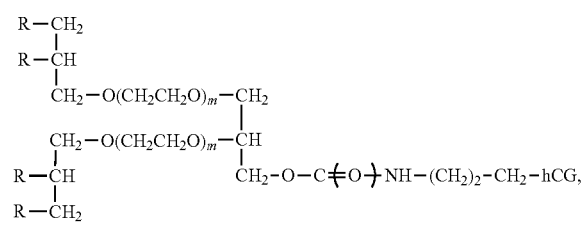

wherein each R is a polyethylene glycol (PEG) or a methoxypolyethylene glycol (mPEG), and m is an integer in the range from 1 to 20.

3. A polyethylene glycol modified human chorionic gonadotrophin (hCG) according to the following formula:

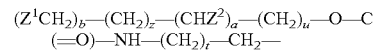
$$(R)_n—X—Y \qquad (Ia)$$

wherein:

X is a linking group comprising a moiety according to the following formula:

$$(Z^1CH_2)_b—(CH_2)_z—(CHZ^2)_a—(CH_2)_u—O—C(=O)—NH—(CH_2)_t—CH_2—$$

a and b are each independently selected from 0 and 1 provided that a and b are not both 0;

t, u and z are each independently 0 or an integer in the range from 1 to 10, and $Z^1$ and $Z^2$ each represent a bond to an R group, or $Z^1$ and $Z^2$ are each independently selected from groups of the formula:

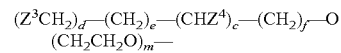
$$(Z^3CH_2)_d—(CH_2)_e—(CHZ^4)_c—(CH_2)_f—O(CH_2CH_2O)_m—$$

$Z^3$ and $Z^4$ each represent a bond to an R group;
c and d are each independently selected from 0 and 1;
e and f are each independently 0 or an integer in the range from 1 to 10, and
m is an integer in the range from 1 to 20;
each R is a polyethylene glycol (PEG) or a methoxypolyethylene glycol (mPEG) group;
n is 2, 3 or 4; and
Y is human chorionic gonadotrophin (hCG).

4. A polyethylene glycol modified hCG according to claim 3, wherein the hCG is recombinant hCG.

5. A polyethylene glycol modified hCG according to claim 3, wherein the hCG is a human cell line-derived recombinant hCG.

6. A polyethylene glycol modified hCG according to claim 3, wherein the hCG is a recombinant hCG (rhCG) including α2,3- and α2,6-sialylation.

7. A polyethylene glycol modified hCG according to claim 3, wherein the hCG is a recombinant hCG having a sialic acid content of 15 moles of sialic acid or greater per mole of hCG protein.

8. A polyethylene glycol modified hCG according to claim 3, wherein the hCG is a recombinant hCG comprising sialylation, wherein 10% or more of the total sialylation is α2,3-sialylation.

9. A polyethylene glycol modified hCG according to claim 3, wherein the hCG is a recombinant hCG comprising sialylation, wherein 45% to 80% of the total sialylation is α2,3-sialylation.

10. A polyethylene glycol modified hCG according to claim 3, wherein the hCG is a recombinant hCG comprising sialylation, wherein 20% to 55% of the total sialylation is α2,6-sialylation.

11. A polyethylene glycol modified hCG according to claim 3, wherein a polyethylene glycol or methoxypolyethylene glycol is conjugated to an amino acid residue of the hCG.

12. A polyethylene glycol modified hCG according to claim 3, wherein a polyethylene glycol or methoxypolyethylene glycol is conjugated to the N-terminus or the C-terminus of the hCG.

13. A polyethylene glycol modified hCG according to claim 3, wherein the polyethylene glycol or methoxypolyethylene glycol is conjugated to the N-terminus of the hCG.

14. A polyethylene glycol modified hCG according to claim 3, wherein the hCG is a recombinant hCG having a sialic acid content in the range from 15 to 25 moles of sialic acid per mole of hCG protein.

15. A polyethylene glycol modified hCG according to claim 3, wherein the hCG is a recombinant hCG comprising sialylation, wherein 50% or less of the total sialylation is α2,6-sialylation.

16. A polyethylene glycol modified hCG according to claim 3, wherein the hCG is a recombinant hCG comprising sialylation, wherein 10% or more of the total sialylation is α2,3-sialylation and 50% or less of the total sialylation is α2,6-sialylation.

17. A polyethylene glycol modified hCG according to claim 3, wherein a, b and u are 1, t is 0 and z is 0.

18. A polyethylene glycol modified hCG according to claim 3, wherein a, b and u are 1, t is 2 and z is 0.

19. A polyethylene glycol modified hCG according to claim 3, wherein $Z^1$ and $Z^2$ are each groups of the formula $(Z^3CH_2)_d-(CH_2)_e-(CHZ^4)_c-(CH_2)_f-O(CH_2CH_2O)_m-$, c, d and f are 1 and e is 0.

20. A polyethylene glycol modified hCG according to claim 3, comprising hCG modified with a 2-arm or a 4-arm branched methoxypolyethylene glycol moiety, wherein:
the 2-arm branched methoxypolyethylene glycol moiety is of the following formula:

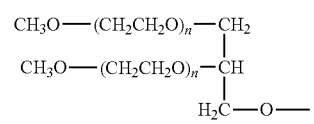

the 4-arm branched methoxypolyethylene glycol moiety is of the following formula:

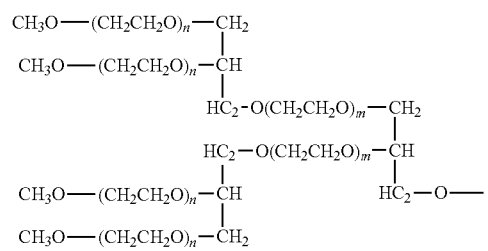

wherein:
each m is an integer and $(CH_2CH_2O)_m$ represents repeating units of a polyethylene glycol polymer;
each n is an integer wherein $(CH_2CH_2O)_n$ represents repeating units of a polyethylene glycol polymer.

21. A polyethylene glycol modified hCG according to claim 20, comprising hCG modified with the 2-arm branched methoxypolyethylene glycol moiety.

22. A polyethylene glycol modified hCG according to claim 21, wherein the modified hCG is of the following formula

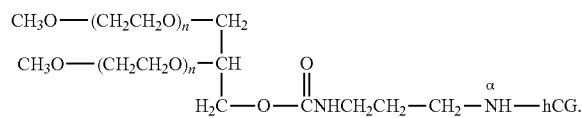

23. A polyethylene glycol modified hCG according to claim 20, comprising hCG modified with the 4-arm branched methoxypolyethylene glycol moiety.

24. A polyethylene glycol modified hCG according to claim 23, wherein the modified hCG is of the following formula

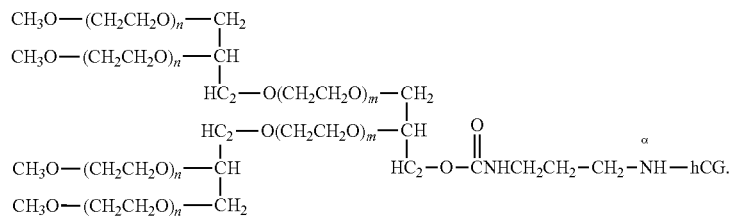

25. A pharmaceutical composition comprising a polyethylene glycol modified hCG according to claim 3.

26. A pharmaceutical composition according to claim 25, further comprising follicle stimulating hormone (FSH) or luteinizing hormone (LH), or both FSH and LH.

27. A method of treatment of infertility comprising a step of administering to a subject a composition comprising a polyethylene glycol modified hCG according to claim 3.

* * * * *

UNITED STATES PATENT AND TRADEMARK OFFICE
CERTIFICATE OF CORRECTION

PATENT NO. : 9,757,469 B2
APPLICATION NO. : 14/008067
DATED : September 12, 2017
INVENTOR(S) : Cottingham et al.

It is certified that error appears in the above-identified patent and that said Letters Patent is hereby corrected as shown below:

In the Specification

After the paragraph ending at Column 21, Line 21, please delete Scheme 1:

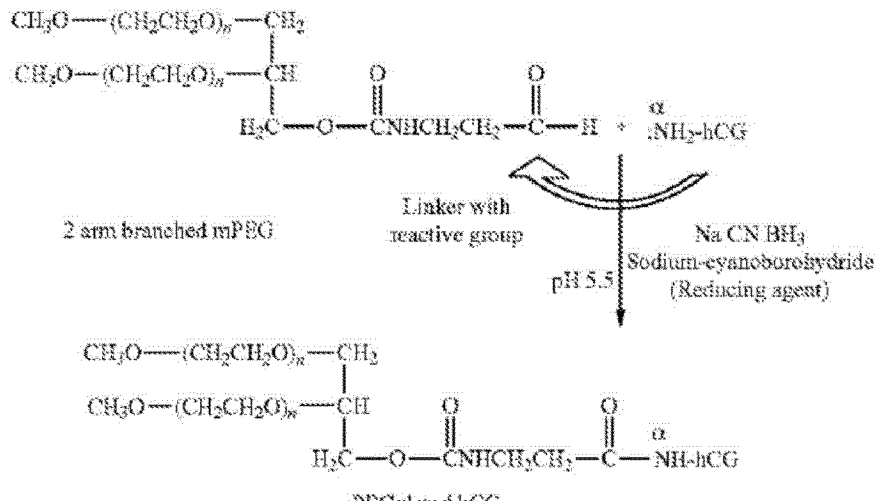

And insert:

Signed and Sealed this
Seventh Day of January, 2020

Andrei Iancu
*Director of the United States Patent and Trademark Office*

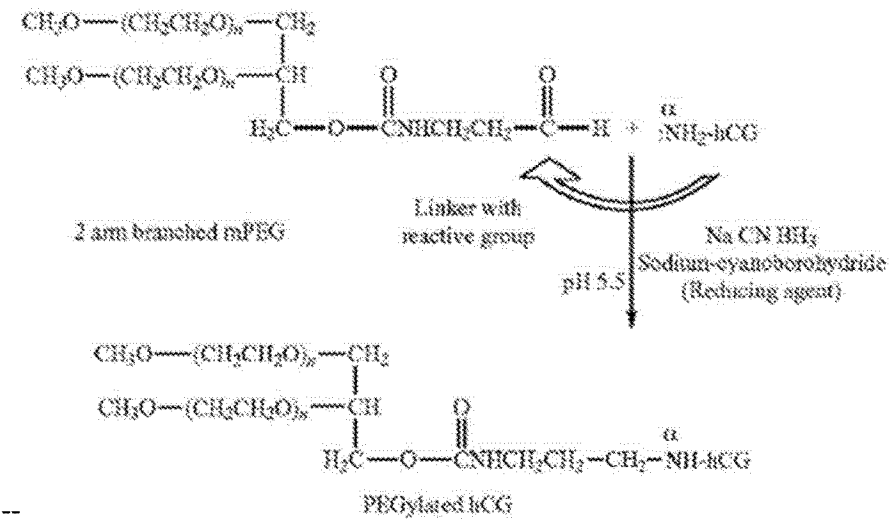
After the paragraph ending at Column 23, Line 22, please delete Scheme 2:
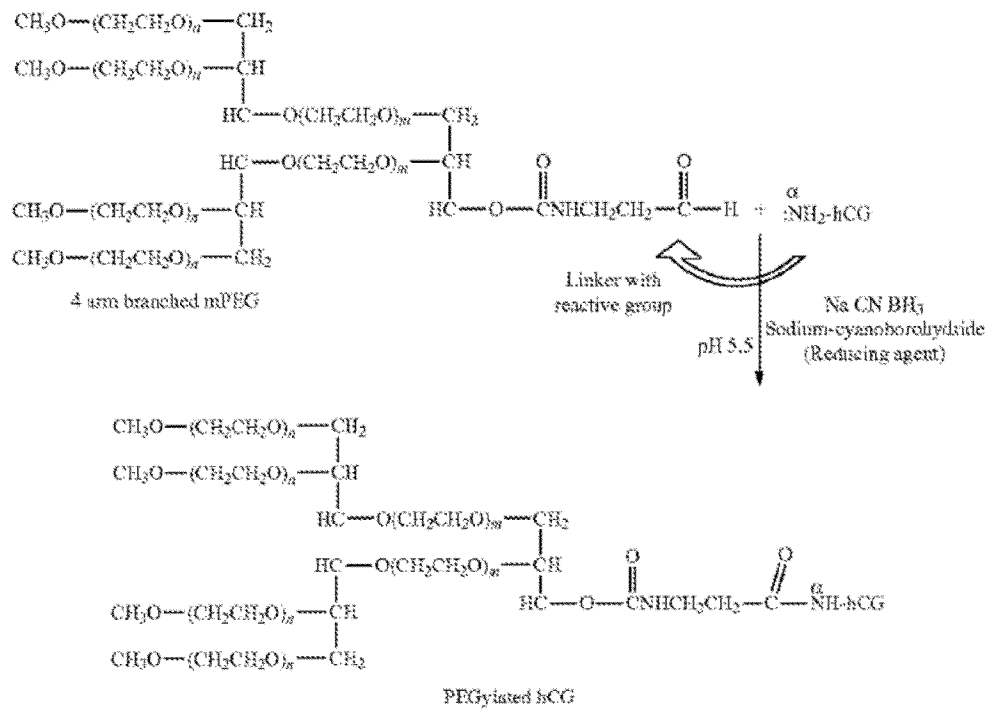
And insert:

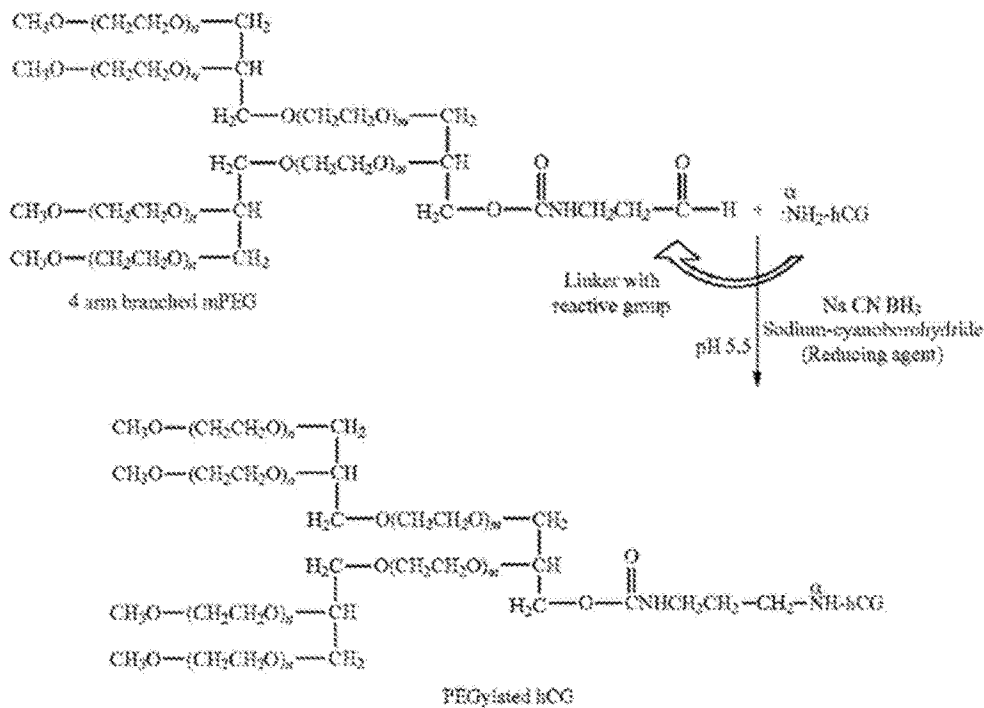
After the paragraph ending at Column 25, Line 7, please delete Scheme 3:
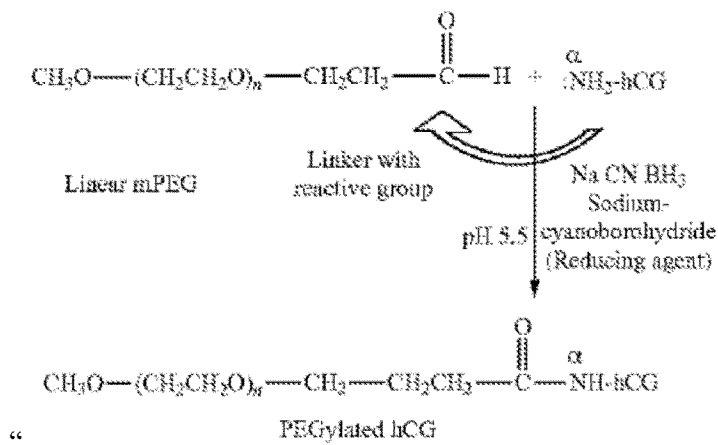
And insert:

CERTIFICATE OF CORRECTION (continued)
U.S. Pat. No. 9,757,469 B2

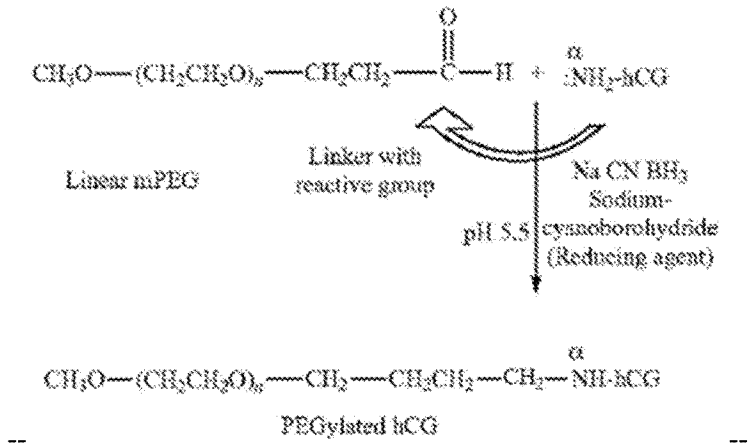

In the Claims

In Claim 20, after "the 4-arm branched methoxypolyethylene glycol moiety is of the following formula," at Column 46, Line 23, please delete the following formula:

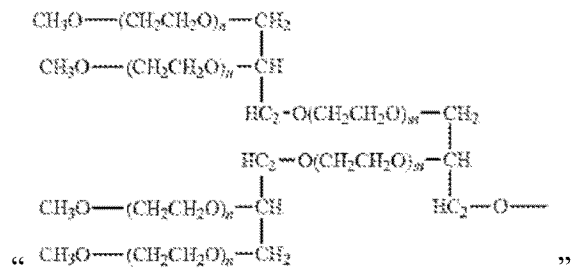

And insert:

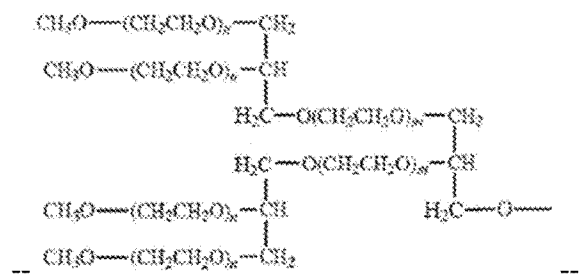

In Claim 24, after "formula," at Column 47, Line 1, please delete the following formula:

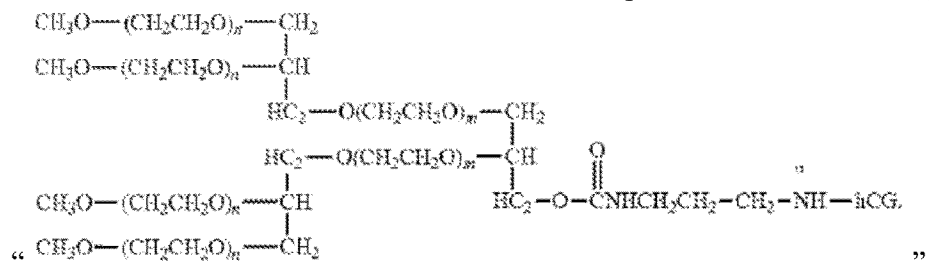

CERTIFICATE OF CORRECTION (continued)
U.S. Pat. No. 9,757,469 B2

And insert:

SEQUENCE LISTING

<160> NUMBER OF SEQ ID NOS: 16

<210> SEQ ID NO 1
<211> LENGTH: 351
<212> TYPE: DNA
<213> ORGANISM: Homo sapiens

<400> SEQUENCE: 1
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatgggggg tttcaaagtg     300
gagaaccaca cggcgtgcca ctgcagtact tgttattatc acaaatctta a             351

<210> SEQ ID NO 2
<211> LENGTH: 116
<212> TYPE: PRT
<213> ORGANISM: Homo sapiens

<400> SEQUENCE: 2

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu

```
                65                  70                  75                  80
Ser Thr Cys Cys Val Ala Lys Ser Tyr Asn Arg Val Thr Val Met Gly
                    85                  90                  95

Gly Phe Lys Val Glu Asn His Thr Ala Cys His Cys Ser Thr Cys Tyr
                100                 105                 110

Tyr His Lys Ser
            115

<210> SEQ ID NO 3
<211> LENGTH: 498
<212> TYPE: DNA
<213> ORGANISM: Homo sapiens

<400> SEQUENCE: 3
atggagatgt tccaggggct gctgctgttg ctgctgctga gcatgggcgg gacatgggca      60
tccaaggagc cgcttcggcc acggtgccgc cccatcaatg ccaccctggc tgtggagaag     120
gagggctgcc ccgtgtgcat caccgtcaac accaccatct gtgccggcta ctgccccacc     180
atgacccgcg tgctgcaggg ggtcctgccg gccctgcctc aggtggtgtg caactaccgc     240
gatgtgcgct tcgagtccat ccggctccct ggctgcccgc gcggcgtgaa ccccgtggtc     300
tcctacgccg tggctctcag ctgtcaatgt gcactctgcc gccgcagcac cactgactgc     360
gggggtccca aggaccaccc cttgacctgt gatgaccccc gcttccagga ctcctcttcc     420
tcaaaggccc ctccccccag ccttccaagt ccatcccgac tcccggggcc ctcggacacc     480
ccgatcctcc cacaataa                                                    498

<210> SEQ ID NO 4
<211> LENGTH: 165
<212> TYPE: PRT
<213> ORGANISM: Homo sapiens

<400> SEQUENCE: 4

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
                35                  40                  45

Val Asn Thr Thr Ile Cys Ala Gly Tyr Cys Pro Thr Met Thr Arg Val
            50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                    85                  90                  95

Asn Pro Val Val Ser Tyr Ala Val Ala Leu Ser Cys Gln Cys Ala Leu
                100                 105                 110

Cys Arg Arg Ser Thr Thr Asp Cys Gly Gly Pro Lys Asp His Pro Leu
            115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165
```

<210> SEQ ID NO 5
<211> LENGTH: 999
<212> TYPE: DNA
<213> ORGANISM: Homo sapiens

<400> SEQUENCE: 5

```
atgtgtcctg caggctggaa gctcctggcc atgttggctc tggtcctggt cgtcatggtg      60
tggtattcca tctcccggga agacaggtac atcgagcttt tttatttttcc catcccagag     120 aagaaggagc cgtgcctcca gggtgaggca gagagcaagg cctctaagct ctttggcaac     180
tactcccggg atcagcccat cttcctgcgg cttgaggatt atttctgggt caagacgcca     240
tctgcttacg agctgcccta tgggaccaag gggagtgagg atctgctcct ccgggtgcta     300
gccatcacca gctcctccat ccccaagaac atccagagcc tcaggtgccg ccgctgtgtg     360
gtcgtgggga acgggcaccg gctgcggaac agctcactgg gagatgccat caacaagtac     420
gatgtggtca tcagattgaa caatgcccca gtggctggct atgagggtga cgtgggctcc     480
aagaccacca tgcgtctctt ctaccctgaa tctgcccact tcgaccccaa agtagaaaac     540
aacccagaca cactcctcgt cctggtagct ttcaaggcaa tggacttcca ctggattgag     600
accatcctga gtgataagaa gcgggtgcga aagggtttct ggaaacagcc tcccctcatc     660
tgggatgtca atcctaaaca gattcggatt ctcaaccct tcttcatgga gattgcagct     720
gacaaactgc tgagcctgcc aatgcaacag ccacggaaga ttaagcagaa gcccaccacg     780
ggcctgttgg ccatcacgct ggccctccac ctctgtgact tggtgcacat tgccggcttt     840
ggctacccag acgcctacaa caagaagcag accattcact actatgagca gatcacgctc     900
aagtccatgg cggggtcagg ccataatgtc tcccaagagg ccctggccat taagcggatg     960
ctggagatgg gagctatcaa gaacctcacg tccttctga                            999
```

<210> SEQ ID NO 6
<211> LENGTH: 332
<212> TYPE: PRT
<213> ORGANISM: Homo sapiens

<400> SEQUENCE: 6

```
Met Cys Pro Ala Gly Trp Lys Leu Leu Ala Met Leu Ala Leu Val Leu
 1               5                  10                  15

Val Val Met Val Trp Tyr Ser Ile Ser Arg Glu Asp Arg Tyr Ile Glu
                20                  25                  30

Leu Phe Tyr Phe Pro Ile Pro Glu Lys Lys Glu Pro Cys Leu Gln Gly
            35                  40                  45

Glu Ala Glu Ser Lys Ala Ser Lys Leu Phe Gly Asn Tyr Ser Arg Asp
        50                  55                  60

Gln Pro Ile Phe Leu Arg Leu Glu Asp Tyr Phe Trp Val Lys Thr Pro
 65                  70                  75                  80

Ser Ala Tyr Glu Leu Pro Tyr Gly Thr Lys Gly Ser Glu Asp Leu Leu
                85                  90                  95
```

```
Leu Arg Val Leu Ala Ile Thr Ser Ser Ile Pro Lys Asn Ile Gln
            100                 105                 110

Ser Leu Arg Cys Arg Arg Cys Val Val Gly Asn Gly His Arg Leu
        115                 120                 125

Arg Asn Ser Ser Leu Gly Asp Ala Ile Asn Lys Tyr Asp Val Ile
    130                 135                 140

Arg Leu Asn Asn Ala Pro Val Ala Gly Tyr Glu Gly Asp Val Gly Ser
145                 150                 155                 160

Lys Thr Thr Met Arg Leu Phe Tyr Pro Glu Ser Ala His Phe Asp Pro
                165                 170                 175

Lys Val Glu Asn Asn Pro Asp Thr Leu Leu Val Leu Val Ala Phe Lys
            180                 185                 190

Ala Met Asp Phe His Trp Ile Glu Thr Ile Leu Ser Asp Lys Lys Arg
        195                 200                 205

Val Arg Lys Gly Phe Trp Lys Gln Pro Pro Leu Ile Trp Asp Val Asn
    210                 215                 220

Pro Lys Gln Ile Arg Ile Leu Asn Pro Phe Phe Met Glu Ile Ala Ala
225                 230                 235                 240

Asp Lys Leu Leu Ser Leu Pro Met Gln Gln Pro Arg Lys Ile Lys Gln
                245                 250                 255

Lys Pro Thr Thr Gly Leu Leu Ala Ile Thr Leu Ala Leu His Leu Cys
            260                 265                 270

Asp Leu Val His Ile Ala Gly Phe Gly Tyr Pro Asp Ala Tyr Asn Lys
        275                 280                 285

Lys Gln Thr Ile His Tyr Tyr Glu Gln Ile Thr Leu Lys Ser Met Ala
    290                 295                 300

Gly Ser Gly His Asn Val Ser Gln Glu Ala Leu Ala Ile Lys Arg Met
305                 310                 315                 320

Leu Glu Met Gly Ala Ile Lys Asn Leu Thr Ser Phe
                325                 330

<210> SEQ ID NO 7
<211> LENGTH: 1221
<212> TYPE: DNA
<213> ORGANISM: Homo sapiens

<400> SEQUENCE: 7
atgattcaca ccaacctgaa gaaaaagttc agctgctgcg tcctggtctt tcttctgttt     60
gcagtcatct gtgtgtggaa ggaaaagaag aaagggagtt actatgattc ctttaaattg    120
caaaccaagg aattccaggt gttaaagagt ctggggaaat ggccatgggg gtctgattcc    180
cagtctgtat cctcaagcag cacccaggac ccccacaggg gccgccagac cctcggcagt    240
ctcagaggcc tagccaaggc caaaccagag gcctccttcc aggtgtggaa caaggacagc    300
tcttccaaaa accttatccc taggctgcaa aagatctgga gaattaccct aagcatgaac    360
aagtacaaag tgtcctacaa ggggccagga ccaggcatca agttcagtgc agaggccctg    420
cgctgccacc tccgggacca tgtgaatgta tccatggtag aggtcacaga tttttccttc    480
```

```
aatacctctg aatgggaggg ttatctgccc aaggagagca ttaggaccaa ggctgggcct      540
tggggcaggt gtgctgttgt gtcgtcagcg ggatctctga agtcctccca actaggcaga      600
gaaatcgatg atcatgacgc agtcctgagg tttaatgggg cacccacagc caacttccaa      660
caagatgtgg gcacaaaaac taccattcgc ctgatgaact ctcagttggt taccacagag      720
aagcgcttcc tcaaagacag tttgtacaat gaaggaatcc taattgtatg ggacccatct      780
gtataccact cagatatccc aaagtggtac cagaatccgg attataattt ctttaacaac      840
tacaagactt atcgtaagct gcaccccaat cagccctttt acatcctcaa gccccagatg      900
ccttgggagc tatgggacat tcttcaagaa atctccccag aagagattca gccaaacccc      960
ccatcctctg ggatgcttgg tatcatcatc atgatgacgc tgtgtgacca ggtggatatt     1020
tatgagttcc tcccatccaa gcgcaagact gacgtgtgct actactacca gaagttcttc     1080
gatagtgcct gcacgatggg tgcctaccac ccgctgctct atgagaagaa tttggtgaag     1140
catctcaacc agggcacaga tgaggacatc tacctgcttg aaaagccac actgcctggc     1200 ttccggacca ttcactgcta a                                               1221
```

<210> SEQ ID NO 8
<211> LENGTH: 406
<212> TYPE: PRT
<213> ORGANISM: Homo sapiens

<400> SEQUENCE: 8

```
Met Ile His Thr Asn Leu Lys Lys Phe Ser Cys Cys Val Leu Val
1               5                   10                  15

Phe Leu Leu Phe Ala Val Ile Cys Val Trp Lys Glu Lys Lys Gly
                20                  25                  30

Ser Tyr Tyr Asp Ser Phe Lys Leu Gln Thr Lys Glu Phe Gln Val Leu
                35                  40                  45

Lys Ser Leu Gly Lys Leu Ala Met Gly Ser Asp Ser Gln Ser Val Ser
        50                  55                  60

Ser Ser Thr Gln Asp Pro His Arg Gly Arg Gln Thr Leu Gly Ser
65                  70                  75                  80

Leu Arg Gly Leu Ala Lys Ala Lys Pro Glu Ala Ser Phe Gln Val Trp
                85                  90                  95

Asn Lys Asp Ser Ser Lys Asn Leu Ile Pro Arg Leu Gln Lys Ile
                100                 105                 110

Trp Lys Asn Tyr Leu Ser Met Asn Lys Tyr Lys Val Ser Tyr Lys Gly
                115                 120                 125

Pro Gly Pro Gly Ile Lys Phe Ser Ala Glu Ala Leu Arg Cys His Leu
        130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
                180                 185                 190

Leu Lys Ser Ser Gln Leu Gly Arg Glu Ile Asp His Asp Ala Val
        195                 200                 205

Leu Arg Phe Asn Gly Ala Pro Thr Ala Asn Phe Gln Gln Asp Val Gly
        210                 215                 220

Thr Lys Thr Thr Ile Arg Leu Met Asn Ser Gln Leu Val Thr Thr Glu
225                 230                 235                 240
```

-continued

```
Lys Arg Phe Leu Lys Asp Ser Leu Tyr Asn Glu Gly Ile Leu Ile Val
                245                 250                 255

Trp Asp Pro Ser Val Tyr His Ser Asp Ile Pro Lys Trp Tyr Gln Asn
            260                 265                 270

Pro Asp Tyr Asn Phe Phe Asn Asn Tyr Lys Thr Tyr Arg Lys Leu His
        275                 280                 285

Pro Asn Gln Pro Phe Tyr Ile Leu Lys Pro Gln Met Pro Trp Glu Leu
    290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                325                 330                 335

Gln Val Asp Ile Tyr Glu Phe Leu Pro Ser Lys Arg Lys Thr Asp Val
            340                 345                 350

Cys Tyr Tyr Tyr Gln Lys Phe Phe Asp Ser Ala Cys Thr Met Gly Ala
        355                 360                 365

Tyr His Pro Leu Leu Tyr Glu Lys Asn Leu Val Lys His Leu Asn Gln
    370                 375                 380

Gly Thr Asp Glu Asp Ile Tyr Leu Leu Gly Lys Ala Thr Leu Pro Gly
385                 390                 395                 400

Phe Arg Thr Ile His Cys
                405
```

<210> SEQ ID NO 9
<211> LENGTH: 39
<212> TYPE: DNA
<213> ORGANISM: Artificial Sequence
<220> FEATURE:
<223> OTHER INFORMATION: Primer CGa-fw

<400> SEQUENCE: 9
ccaggatccg ccaccatgga ttactacaga aaaatatgc         39

<210> SEQ ID NO 10
<211> LENGTH: 31
<212> TYPE: DNA
<213> ORGANISM: Artificial Sequence
<220> FEATURE:
<223> OTHER INFORMATION: Primer CGa-rev

<400> SEQUENCE: 10
ggatggctag cttaagattt gtgataataa c         31

<210> SEQ ID NO 11
<211> LENGTH: 36
<212> TYPE: DNA
<213> ORGANISM: Artificial Sequence
<220> FEATURE:
<223> OTHER INFORMATION: Primer CGb-fw

<400> SEQUENCE: 11
ccaggcgcgc caccatggag atgttccagg ggctgc         36

<210> SEQ ID NO 12
<211> LENGTH: 30
<212> TYPE: DNA
<213> ORGANISM: Artificial Sequence
<220> FEATURE:
<223> OTHER INFORMATION: Primer CGb-rev

<400> SEQUENCE: 12

```
ccgggttaac ttattgtggg aggatcgggg                                        30

<210> SEQ ID NO 13
<211> LENGTH: 37
<212> TYPE: DNA
<213> ORGANISM: Artificial Sequence
<220> FEATURE:
<223> OTHER INFORMATION: Primer 2,3STfw

<400> SEQUENCE: 13
ccaggatccg ccaccatgtg tcctgcaggc tggaagc                                37

<210> SEQ ID NO 14
<211> LENGTH: 35
<212> TYPE: DNA
<213> ORGANISM: Artificial Sequence
<220> FEATURE:
<223> OTHER INFORMATION: Primer 2,3STrev

<400> SEQUENCE: 14
ttttttcctt aagtcagaag gacgtgaggt tcttg                                  35

<210> SEQ ID NO 15
<211> LENGTH: 36
<212> TYPE: DNA
<213> ORGANISM: Artificial Sequence
<220> FEATURE:
<223> OTHER INFORMATION: Primer 2,6STfw

<400> SEQUENCE: 15
ccaggatccg ccaccatgat tcacaccaac ctgaag                                 36

<210> SEQ ID NO 16
<211> LENGTH: 32
<212> TYPE: DNA
<213> ORGANISM: Artificial Sequence
<220> FEATURE:
<223> OTHER INFORMATION: Primer 2,6STrev

<400> SEQUENCE: 16
ttttttcctt aagttagcag tgaatggtcc gg                                     32
```